(12) United States Patent
Li et al.

(10) Patent No.: US 8,188,091 B2
(45) Date of Patent: May 29, 2012

(54) TETRAHYDROQUINAZOLINE COMPOUNDS AND THEIR USE IN PREPARING MEDICAMENTS FOR TREATING AND PREVENTING VIROSIS

(75) Inventors: Song Li, Beijing (CN); Xuejun Zhu, Beijing (CN); Guoming Zhao, Beijing (CN); Lili Wang, Beijing (CN); Wu Zhong, Beijing (CN); Zhibing Zheng, Beijing (CN); Junhai Xiao, Beijing (CN)

(73) Assignee: Beijing Molecule Science and Technology Co., Ltd., Beijing (CN)

( * ) Notice: Subject to any disclaimer, the term of this patent is extended or adjusted under 35 U.S.C. 154(b) by 242 days.

(21) Appl. No.: 12/523,215

(22) PCT Filed: Jan. 3, 2008

(86) PCT No.: PCT/CN2008/000023
§ 371 (c)(1), (2), (4) Date: Nov. 23, 2009

(87) PCT Pub. No.: WO2008/086730
PCT Pub. Date: Jul. 24, 2008

(65) Prior Publication Data
US 2010/0075988 A1    Mar. 25, 2010

(30) Foreign Application Priority Data
Jan. 16, 2007    (CN) .......................... 2007 1 0000689

(51) Int. Cl.
*A61K 31/4965* (2006.01)
*C07D 401/00* (2006.01)

(52) U.S. Cl. .............. 514/255.05; 514/266.21; 544/284; 544/283

(58) Field of Classification Search ............. 514/255.05, 514/266.21; 544/284, 283
See application file for complete search history.

(56) References Cited

U.S. PATENT DOCUMENTS
7,671,059 B2 *  3/2010  Machajewski et al. .. 514/255.05
2007/0027150 A1  2/2007  Bellamacina et al.

FOREIGN PATENT DOCUMENTS
| | | |
|---|---|---|
| CN | 1071917 | 5/1993 |
| JP | 57 11970 | 1/1982 |
| WO | WO 00/58302 A1 | 10/2000 |
| WO | WO 01/68642 A1 | 9/2001 |
| WO | WO 2006/048308 A1 | 5/2006 |
| WO | 2006 113498 | 10/2006 |
| WO | WO 2006/113498 A2 | 10/2006 |

* cited by examiner

*Primary Examiner* — Rei-tsang Shiao
(74) *Attorney, Agent, or Firm* — Oblon, Spivak, McClelland, Maier & Neustadt, L.L.P.

(57) ABSTRACT

The present invention relates to a compound of formula (I) or isomers thereof, or pharmaceutically acceptable salts or hydrates thereof. The present invention further relates to processes for the preparation of the compounds of formula (I) and optical isomers, and to the use of the compounds of formula (I), or isomers thereof, or pharmaceutically acceptable salts or hydrates thereof as medicaments, in particular as medicaments for the treatment and prevention of Hepatitis B.

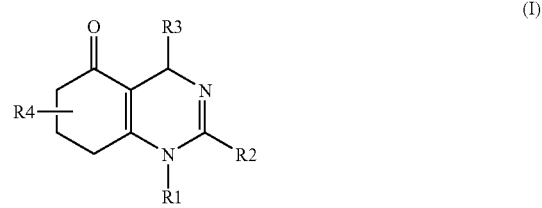

(I)

17 Claims, No Drawings

TETRAHYDROQUINAZOLINE COMPOUNDS AND THEIR USE IN PREPARING MEDICAMENTS FOR TREATING AND PREVENTING VIROSIS

CROSS-REFERENCE TO RELATED APPLICATIONS

This application is a 371 of PCT/CN08/000023 filed Jan. 3, 2008 and claims the benefit of China 200710000689.8 filed Jan. 16, 2007.

TECHNICAL FIELD

The present invention relates to a tetrahydroquinazolinone compound of formula (I), a process for preparing the same, a pharmaceutical composition comprising the compound, and the use of the compound, or a isomer, a pharmaceutically acceptable salt or a hydrate thereof as a medicament, in particular as a medicament for the treatment and prevention of Hepatitis B.

BACKGROUND ART

Chronic Hepatitis B is a severe infectious disease widely prevalent throughout the world, which is caused by hepatitis B virus (HBV) and is closely associated with occurrence of hepatocirrhosis and liver cancer. China is a high prevalence area of Hepatitis B. The results of nationally seropidemiological survey of viral hepatitis in China from 1992 to 1995 showed that the persons carrying viral hepatitis B surface antigen (HBsAg) in China accounted for 9.7% of the population, and it was estimated that there are $1.3 \times 10^8$ HBV carriers. The study on the epidemic situation of viral hepatitis in China showed that the annual reported morbidity of hepatitis B increased from 21.9/100,000 in 1990 to 53.3/100,000 in 2003, which exhibited an obvious ascending trendency (see: Wang Xiaojun, Zhang Rongzhen and Hu Yuansheng et al, Disease Monitoring, 2004, 19(8): 290-292). Chronic Hepatitis B not only seriously affects the health of human body but also imposes heavy economic burden on family and society. Chronic Hepatitis B has become one of significant public health problems in China.

Drugs for the treatment of Chronic Hepatitis B usually belong to two main classes, i.e. immunomodulators and nucleoside DNA polymerase inhibitors (Loomba R., Liang T. J., Antivir. Ther., 2006, 11(1): 1-15), in which the former includes interferon-α2b (IFN-α2b, Intron A®) and Pegylated interferon-α2a (peg IFN-α2a, Pegasys®), while the latter includes Lamivudine (EPivir-HBV®), Adefovir Dipivoxil (Hepsera®) and Entecavir (Baraclude®). Comparatively speaking, there are quite few of drugs in number and class for the clinical treatment of Hepatitis B. Therefore, it is of high significance to research and develop novel, safe and effective antiviral drugs, in particular those having a completely new mechanism of action.

Quinazolinone compounds have a wide range of physiological activities, for example, they can be used as adrenoceptor regulators (WO2005005397) and estrogen receptor regulators (WO2006116401). In the meantime, 2(1H)- and 4(1H)-quinazolinone compounds further have activities such as pyretolysis, analgesic and anti-inflammatory activity (GB1308198, U.S. Pat. No. 3,895,395, JP57011970), and 4(3H)-quinazolinone compounds have anti-ulcer activity (EP0276826). However, no report has been found relating to 5(1H)-quinazolinone compounds.

CONTENTS OF THE INVENTION

The present invention relates to a tetrahydroquinazolinone compound of formula (I), or its isomer, pharmaceutically acceptable salt or hydrate,

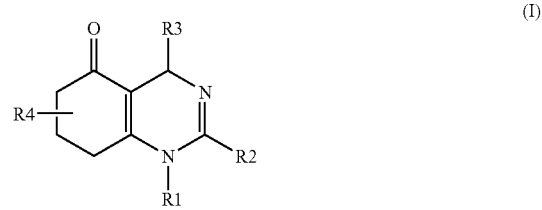

wherein,
$R^1$ represents hydrogen, a $(C_1\text{-}C_4)$-alkyl, a $(C_2\text{-}C_4)$-alkenyl, a $(C_2\text{-}C_6)$-acyl, a sulfonyl or benzoyl, $R^2$ represents a 5- or 6-membered aryl or heteroaryl mono-substituted or multiple-substituted with the same or different substituents selected from: hydrogen, halogen, hydroxyl, cyano, trifluoromethyl, nitro, benzyl, a $(C_1\text{-}C_6)$-alkyl, a $(C_1\text{-}C_6)$-alkoxyl, a $(C_1\text{-}C_6)$-alkylthio, a $(C_1\text{-}C_6)$-alkoxylcarbonyl, a $(C_1\text{-}C_6)$-acyloxy, amino, a $(C_1\text{-}C_6)$-alkylamino, a $(C_1\text{-}C_6)$-dialkylamino, or a $(C_1\text{-}C_6)$-acylamino, $R^3$ represents an aryl or heteroaryl mono-substituted or multiple-substituted with the same or different substituents selected from: hydrogen, halogen, trifluoromethyl, trifluoromethoxyl, trifluoromethanesulfonyl, nitro, cyano, carboxyl, hydroxyl, a $(C_1\text{-}C_6)$-alkoxyl, a $(C_1\text{-}C_6)$-alkoxycarbonyl or a $(C_1\text{-}C_6)$-alkyl, wherein the alkyl moiety can be substituted with an aryl having 6-10 carbon atoms, halogen, or a group represented by —S—$R^5$, $NR^6R^7$, CO—$NR^8R^9$ or -A-$CH_2$—$R^{10}$, wherein
$R^5$ represents phenyl which may be optionally substituted with halogen atoms, $R^6$, $R^7$, $R^8$ and $R^9$ each are the same or different, and independently represents hydrogen, phenyl, hydroxyl-substituted phenyl, hydroxyl, a $(C_1\text{-}C_6)$-acyl or a $(C_1\text{-}C_6)$-alkyl, wherein the alkyl moiety can be substituted with hydroxyl, halogen, a $(C_1\text{-}C_6)$-alkoxycarbonyl, phenyl or hydroxyl-substituted phenyl, A represents O, S, SO or $SO_2$, and $R^{10}$ represents phenyl which can be optionally mono- or multiple-substituted with the same or different substituents selected from: halogen, nitro, trifluoromethyl, a $(C_1\text{-}C_6)$-alkyl or a $(C_1\text{-}C_6)$-alkoxy, and $R^4$, for one or more occurrences, each independently represents, a substituent selected from: hydrogen, halogen, nitro, cyano, hydroxyl, a $(C_1\text{-}C_6)$-alkyl, a $(C_1\text{-}C_6)$-alkoxyl, a $(C_1\text{-}C_6)$-alkoxycarbonyl, or an aryl or heteroaryl having 6-10 carbon atoms, wherein the aryl or heteroaryl can be substituted with halogen or a $(C_1\text{-}C_6)$-alkyl.

In the specification of the present application, the term "$(C_2\text{-}C_6)$-alkenyl" refers to a straight or branched alkenyl having 2-6 carbon atoms, preferably having 3-5 carbon atoms, including but not being limited to vinyl, propenyl, n-pentenyl or n-hexenyl.

In the specification of the present application, the term "$(C_2\text{-}C_6)$-acyl" refers to a straight or branched acyl having 2-6 carbon atoms, preferably having 2-4 carbon atoms.

In the specification of the present application, the aryl usually refers to a 5- to 14-membered aromatic ring system, or may comprise a condensed bicyclic or tricyclic aromatic ring system, including but not being limited to phenyl and naphthyl.

In the specification of the present application, the heteroaryl usually refers to a 5- to 14-membered aromatic ring system having heteroatoms such as N, O and S, or may comprise a condensed bicyclic or tricyclic aromatic ring system, including but not being limited to pyridine, pyrazine, furan, thiazole, thiophene, tetrahydroquinazoline or dihydroquinazoline.

In the specification of the present application, the ($C_1$-$C_6$)-alkyl refers to a straight or branched group containing 1-6 carbon atoms, including but not being limited to methyl, ethyl, n-propyl, isopropyl, n-butyl, sec-butyl, iso-butyl or tert-butyl.

In the specification of the present application, the ($C_1$-$C_6$)-alkoxy refers to a straight or branched alkoxy having 1-6 carbon atoms, preferably having 1-4 carbon atoms, including but not limited to methoxy, ethoxy, propoxy, isopropoxy, butoxy, iso-butoxy or tert-butoxy or the like.

In the specification of the present application, the ($C_1$-$C_6$)-alkylthio refers to a straight or branched alkylthio having 1-6 carbon atoms, preferably having 1-4 carbon atoms.

In the specification of the present application, the ($C_1$-$C_6$)-alkoxycarbonyl refers to a straight or branched alkoxycarbonyl having 1-6 carbon atoms, preferably having 1-4 carbon atoms, including but not being limited to methoxycarbonyl, ethoxycarbonyl, propoxycarbonyl, isopropoxycarbonyl, butoxycarbonyl, iso-butoxycarbonyl or tert-butoxycarbonyl or the like.

The compounds of the present invention include the compounds of formula (I) and isomers (Ia) thereof and their mixtures. When $R_1$ is hydrogen, (I) and (Ia) can be in balance of forms of tautomers.

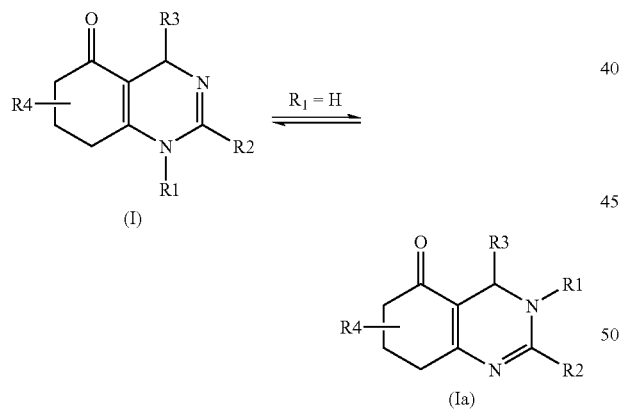

The compound of the present invention can be present in the form of optical isomers. The optical isomers can be enantiomers or diastereoisomers. The present invention relates to these enantiomers or diastereoisomers, as well as their mixtures. Like diastereoisomers, racemates can be resolved by known methods to be single components of optical isomers. For example, the resolution can be performed by forming a salt of an acidic chiral resoluting agent with the basic nitrogen atom in the molecule of the present compound. This method of resolution is described specifically as follows: independently dissolving a compound of the present invention and a resoluting agent in organic solvents, then mixing, standing to precipitate solid, separating the solid from solution, independently treating with basic solutions and extracting them with organic solvents to obtain a pair of enantiomers.

The acidic chiral resoluting agent includes but is not limited to camphanic acid, camphor sulfonic acid of R- or S-configuration, tartaric acid, lactic acid, malic acid, natural or non-natural amino acids of D- or L-configuration, and derivatives thereof.

The organic solvents used in the above resolution process include but are not limited to methanol, ethanol, acetone, ethyl acetate, ethyl ether, petroleum ether, dichloromethane, trichloromethane, etc.

Alternatively, the optically pure enantiomers can be obtained by introducing another chiral group into the molecule of the compound of the present invention in order to form a pair of diastereoisomers prone to be separated, and removing the introduced chiral group after separation and purification. This process is described specifically as follows:

1) Reacting a compound of formula (I) with chloride or anhydride of an acid having at least one chiral center in its molecular in a suitable inert solvent in the presence of a base, or reacting a compound of formula (I) with an acid having at least one chiral center in its molecular in the presence of a suitable condensing agent, to obtain a compound of formula (VII) and a compound of formula (VIII),

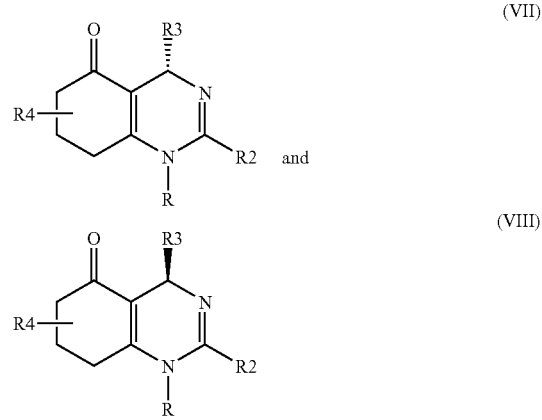

wherein $R^2$, $R^3$, and $R^4$ have the same definitions as above, R represents an acyl or sulfonic group having at least one chiral center, and 2) Reacting the compound of formula (VII) or (VIII) with a strong base such as sodium alkoxide in a suitable solvent to obtain a pair of enantiomers of the compound of formula (I),

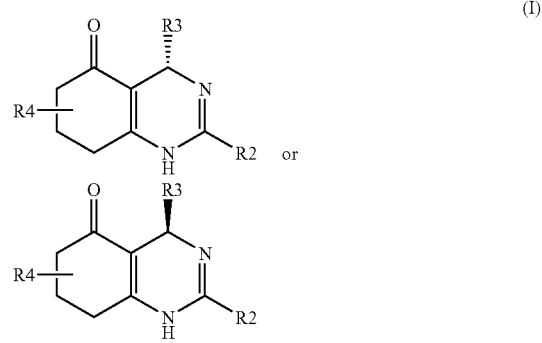

wherein $R^2$, $R^3$, and $R^4$ have the same definitions as above, wherein the acid having at least one chiral center in its molecular includes but is not limited to camphanic acid, camphorsulfonic acid of R- or S-configuration, tartaric acid, lactic acid, malic acid, natural or non-natural amino acids of D- or L-configuration, and derivatives thereof.

The condensing agent includes but is not limited to dicyclohexylcarbodiimide (DCC), diisopropylcarbodiimide (DIC), N,N'-carbonyldiimidazole (CDI), 1-ethyl-3[3-(dimethylamino)propyl]-carbodiimide (EDCI), BOP (Castro's condensing agent), etc.

The chiral resolution of the compounds of the present invention are further illustrated by the following reaction schemes:

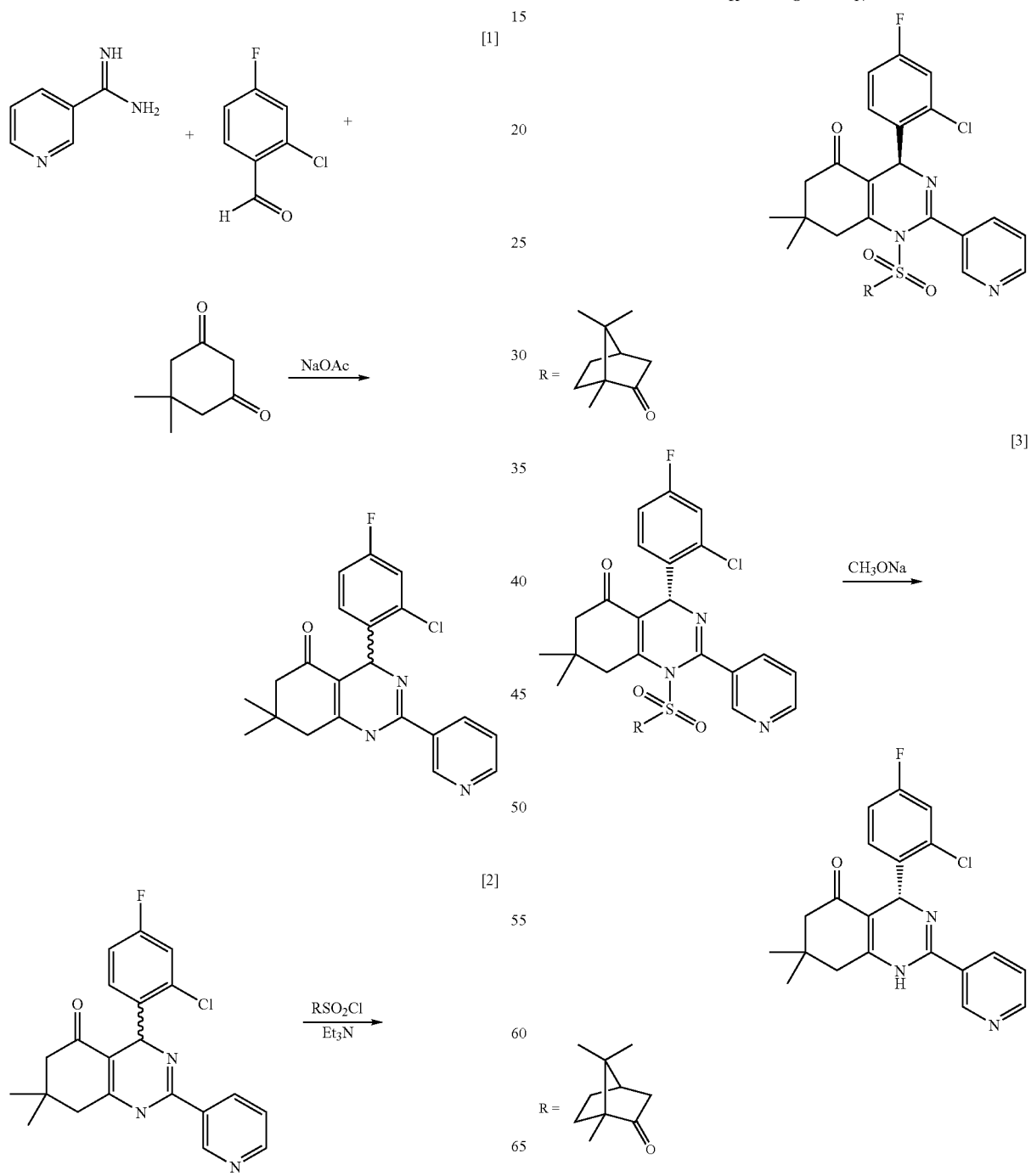

The compound of the present invention may also be in the form of salts, in which pharmaceutically acceptable salts are preferred.

The pharmaceutically acceptable salts of the compound of the present invention include but are not limited to salts formed with inorganic acids, such as hydrochloric acid, sulfuric acid, phosphoric acid, phosphorous acid, hydrobromic acid and nitric acid, and salts formed with various organic acids, such as maleic acid, fumaric acid, malic acid, furmaric acid, succinic acid, tartaric acid, citric acid, acetic acid, lactic acid, benzoic acid, methanesulphonic acid, ethanesulphonic acid, phenylsulphonic acid, para-toluenesulphonic acid or palmitic acid.

The pharmaceutically acceptable salts of the compound of the present invention also include but are not limited to metal salts of the compounds according to the present invention, such as sodium, potassium, magnesium or calcium salts, and ammonium salts formed with ammonia or organic amines such as ethylamine, diethylamine, triethylamine, diethanolamine, triethanolamine, dicyclohexylamine, dimethylaminoethanol, arginine, lysine, ethylenediamine or 2-phenylethylamine.

Some compounds according to the present invention may be crystallized or recrystallized from water or various organic solvents. Under this circumstance, it is possible to form various solvates. The present invention includes stoechiometric solvates, including hydrates and compounds containing variable water formed during the preparation by lyophylization.

Preference is given to the compounds of formula (I) or isomers thereof, and salts or hydrates thereof, in which:

$R^1$ represents hydrogen, methyl, acetyl, benzoyl or methylsulfonyl, $R^2$ represents a 5- or 6-membered aryl or heteroaryl mono-substituted or multiple-substituted with the same or different substituents selected from: hydrogen, fluorine, chlorine, bromine, hydroxyl, cyano, trifluoromethyl, nitro, a $(C_1-C_3)$-alkyl, a $(C_1-C_3)$-alkoxyl, amino, or a $(C_1-C_3)$-acylamino, $R^3$ represents an aryl or heteroaryl mono- or multiple-substituted with the same or different substituents selected from: hydrogen, halogen, trifluoromethyl, trifluoromethoxyl, trifluoromethanesulfonyl, nitro, cyano, carboxyl, hydroxyl, methoxycarbonyl and a group represented by formula —CONHCH$_2$C(CH$_3$)$_3$, —CONH(CH$_2$)$_2$OH, —CONHCH$_2$C$_6$H$_5$, —CONHC$_6$H$_5$, —OCH$_2$C$_6$H$_5$ or —S-pCl—C$_6$H$_4$, and $R^4$, for one or more occurrences, each independently represents a substituent selected from: hydrogen, halogen, nitro, cyano, hydroxyl, a $(C_1-C_3)$-alkyl, a $(C_1-C_3)$-alkoxyl, a $(C_1-C_3)$-alkoxylcarbonyl, an aryl or heteroaryl having 6-10 carbon atoms, wherein the aryl or heteroaryl can be substituted with halogen, or a $(C_1-C_3)$-alkyl.

The compounds of formula (I) or its isomers and their salts or hydrates are particularly preferred, wherein:

$R^1$ represents hydrogen, acetyl or methylsulfonyl, $R^2$ represents furyl, phenyl, pyridyl, or pyrazinyl mono- or multiple-substituted with the same or different substituents selected from: hydrogen, fluorine, chlorine, bromine, trifluoromethyl, a $(C_1-C_3)$-alkyl, a $(C_1-C_3)$-alkoxyl, amino, or a $(C_1-C_3)$-acylamino, $R^3$ represents phenyl mono- or multiple-substituted with the same or different substituents selected from: hydrogen, fluorine, chlorine, bromine, trifluoromethyl, trifluoromethoxyl, trifluoromethanesulfonyl, nitro, cyano, carboxyl, hydroxyl, or methoxycarbonyl, and $R^4$, for one or more occurrences, each independently represents a substituent selected from: hydrogen, fluorine, chlorine, methyl, ethyl, propyl, isopropyl, methoxy, ethoxy, hydroxyl, or phenyl, wherein the phenyl can be substituted with fluorine, chlorine, or a $(C_1-C_3)$-alkyl.

The compounds of formula (I) or its isomers and their salts or hydrates are much particularly preferred, wherein:

$R^1$ represents hydrogen, $R^2$ represents furyl, phenyl, pyridyl, or pyrazinyl mono- or multiple-substituted with the same or different substituents selected from: hydrogen, fluorine, and chlorine, $R^3$ represents phenyl mono- or multiple-substituted with the same or different substituents selected from: hydrogen, chlorine, and fluorine, $R^4$, for one or more occurrences, each independently represents a substituent selected from: hydrogen, and methyl.

The compounds of formula (I) or its isomers and their salts or hydrates as listed as follows are much particularly preferred, (1) 2-(pyridin-3-yl)-4-(2-chloro-4-fluorophenyl)-7,7-dimethyl-4,6,7,8-tetrahydroquinazolin-5(1H)-one, (2) 2-(pyridin-3-yl)-4-(2-chloro-4-fluorophenyl)-7,7-dimethyl-4,6,7,8-tetrahydroquinazolin-5(1H)-one hydrochloride, (3) 2-(pyridin-3-yl)-4-(2-chloro-4-fluorophenyl)-4,6,7,8-tetrahydroquinazolin-5(1H)-one, (4) 2-(pyridin-3-yl)-4-(4-fluorophenyl)-7,7-dimethyl-4,6,7,8-tetrahydroquinazolin-5(1H)-one, (5) 2-(pyridin-3-yl)-4-phenyl-7,7-dimethyl-4,6,7,8-tetrahydroquinazolin-5(1H)-one, (6) 2-(pyridin-3-yl)-4-phenyl-4,6,7,8-tetrahydroquinazolin-5(1H)-one, (7) 2-(pyridin-3-yl)-4-(2-chlorophenyl)-7,7-dimethyl-4,6,7,8-tetrahydroquinazolin-5(1H)-one, (8) 2-(pyridin-3-yl)-4-(4-fluorophenyl)-4,6,7,8-tetrahydroquinazolin-5(1H)-one, (9) 2-(pyridin-3-yl)-4-(2-chlorophenyl)-4,6,7,8-tetrahydroquinazolin-5(1H)-one,

(10) 2-(2,4,6-trifluorophenyl)-4-(2-chloro-4-fluorophenyl)-4,6,7,8-tetrahydroquinazolin-5(1H)-one,

(11) 2-(2,4,6-trifluorophenyl)-4-(2-chloro-4-fluorophenyl)-7,7-dimethyl-4,6,7,8-tetrahydroquinazolin-5(1H)-one,

(12) 2-(pyridin-2-yl)-4-(2-chloro-4-fluorophenyl)-7,7-dimethyl-4,6,7,8-tetrahydroquinazolin-5(1H)-one,

(13) 2-(pyrazin-2-yl)-4-(2-chloro-4-fluorophenyl)-7,7-dimethyl-4,6,7,8-tetrahydro quinazolin-5(1H)-one,

(14) 2-(pyrazin-2-yl)-4-(2-chlorophenyl)-7,7-dimethyl-4,6,7,8-tetrahydroquinazolin-5(1H)-one,

(15) 2-(pyrazin-2-yl)-4-(2-chloro-4-fluorophenyl)-4,6,7,8-tetrahydroquinazolin-5(1H)-one,

(16) 2-(pyrazin-2-yl)-4-(2-chlorophenyl)-4,6,7,8-tetrahydroquinazolin-5(1H)-one,

(17) 2-(3-fluoropyridin-2-yl)-4-(2-chloro-4-fluorophenyl)-7,7-dimethyl-4,6,7,8-tetrahydroquinazolin-5(1H)-one,

(18) 2-(3-fluoropyridin-2-yl)-4-(2-chloro-4-fluorophenyl)-4,6,7,8-tetrahydroquinazolin-5(1H)-one,

(19) 2-(furan-2-yl)-4-(2-chloro-4-fluorophenyl)-7,7-dimethyl-4,6,7,8-tetrahydroquinazolin-5(1H)-one,

(20) 2-(furan-2-yl)-4-(2-chloro-4-fluorophenyl)-4,6,7,8-tetrahydroquinazolin-5(1H)-one,

(21) 2-(pyridin-2-yl)-4-(2-chloro-4-fluorophenyl)-4,6,7,8-tetrahydroquinazolin-5(1H)-one,

(22) 2-(pyridin-2-yl)-4-(2-chlorophenyl)-4,6,7,8-tetrahydroquinazolin-5(1H)-one,

(23) 2-(pyridin-2-yl)-4-(4-fluorophenyl)-4,6,7,8-tetrahydroquinazolin-5(1H)-one,

(24) 2-(pyridin-2-yl)-4-phenyl-4,6,7,8-tetrahydroquinazolin-5(1H)-one,

(25) 2-(thiazol-2-yl)-4-(2-chloro-4-fluorophenyl)-7,7-dimethyl-7,8-dihydroquinazolin-5(1H)-one,
(26) 2-(thiazol-2-yl)-4-(2-chloro-4-fluorophenyl)-7,8-dihydroquinazolin-5(1H)-one,
(27) 2-(thiazol-2-yl)-4-(4-fluorophenyl)-7,8-dihydroquinazolin-5(1H)-one,
(28) 2-(thiazol-2-yl)-4-(2-chlorophenyl)-7,8-dihydroquinazolin-5(1H)-one,
(29) 2-(thiazol-2-yl)-4-(2-chloro-4-fluorophenyl)-7,7-dimethyl-7,8-dihydroquinazolin-5(1H)-one,
(30) 2-(pyridin-4-yl)-4-(2-chloro-4-fluorophenyl)-7,7-dimethyl-7,8-dihydroquinazolin-5(1H)-one,
(31) 2-(pyridin-4-yl)-4-(2-chloro-4-fluorophenyl)-7,8-dihydroquinazolin-5(1H)-one,
(32) 2-(3,5-difluoropyridin-2-yl)-4-(2-chloro-4-fluorophenyl)-7,7-dimethyl-7,8-dihydroquinazolin-5(1H)-one,
(33) 2-(3,5-difluoropyridin-2-yl)-4-(2-chloro-4-fluorophenyl)-7,8-dihydroquinazolin-5(1H)-one,
(34) 2-(3-fluoropyridin-2-yl)-4-(4-fluorophenyl)-7,7-dimethyl-7,8-dihydroquinazolin-5(1H)-one,
(35) 2-(3-fluoropyridin-2-yl)-4-(4-fluorophenyl)-7,8-dihydroquinazolin-5(1H)-one,
(36) 2-(3-fluoropyridin-2-yl)-4-(2-chlorophenyl)-7,8-dihydroquinazolin-5(1H)-one
(37) 2-(thiophen-2-yl)-4-(2-chloro-4-fluorophenyl)-7,7-dimethyl-7,8-dihydroquinazolin-5(1H)-one, or
(38) 2-(thiophen-2-yl)-4-(2-chloro-4-fluorophenyl)-7,8-dihydroquinazolin-5(1H)-one.

The compounds of formula (I) of the present invention can be prepared by the following method:

A) reacting an amidine of formula (II) or a salt thereof

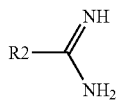
(II)

wherein $R^2$ has the same definition as above,
with an aldehyde of formula (III)

$R^3$CHO (III)

wherein $R^3$ has the same definition as above,
and a compound of formula (IV),

(IV)

wherein $R^4$ has the same definition as above,
in a suitable inert solvent in the presence or absence of a base or an acid;
or
reacting a compound of formula (V) or (VI)

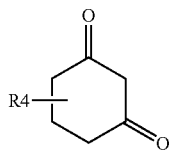
(V)

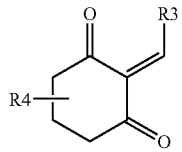
(VI)

wherein $R^3$, $R^4$ have the definition as above,
with the compound of formula (II), at 20-150° C. in a suitable inert solvent in the presence or absence of a base or acid; and B) reacting the product of the previous step with a compound of formula $R^1X$, wherein $R^1$ has the same definition as above, in a suitable inert solvent under basic condition.

The process of the present invention is illustrated by the following reaction scheme:

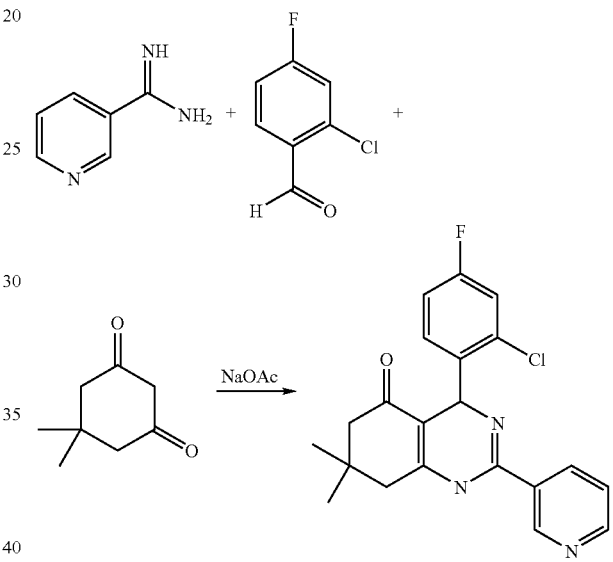

As for the reaction, the suitable solvent is any inert organic solvents. These solvents preferably include alcohols, such as ethanol, menthol, isopropanol, ethers such as dioxane, ethyl ether, tetrahydrofuran, ethylene glycol monomethyl ether, ethylene glycol dimethyl ether, or glacial acetic acid, dimethylformamide, dimethyl sulfoxide, acetonitrile, pyridine, and hexamethyl phosphoramide.

The reaction temperature can vary in a broad range. Usually, the reaction is conducted at a temperature of 20-150° C., and preferably at the boiling point of each solvent.

The reaction can be conducted at normal pressure, but can also be conducted at an elevated pressure. Typically, the reaction is conducted at normal pressure.

The reaction can be conducted in the presence or absence of a base or an acid. Organic acids can be formic acid, glacial acetic acid, methylsulfonic acid, p-toluenesulfonic acid, and inorganic acids can be hydrochloric acid, sulfuric acid, phosphoric acid, nitric acid etc. Preferably, the reaction of the present invention is conducted in the presence of a relatively weak acid, such as acetic acid or formic acid.

The suitable base for the reaction include organic bases such as triethyl amine, methyldiethylamine, pyridine, hexahydropyridine, morpholine, and inorganic bases such as sodium carbonate, potassium carbonate, sodium hydrogen carbonate, sodium acetate, sodium hydroxide, potassium hydroxide.

The amidine of formula (II) as a starting material is known in some circumstances, or can be prepared from a corresponding nitrile compound according to the known methods as recited in the references (see: Diana, G. D., Yarinsky, A., Zalay, E. S., et al. J. Med. Chem. 1969, 12(9): 791-793; Garigipati, R. S. Tetrahedron. Lett. 1990, 31(14): 1969-1972; Boere, R. J., Oakley, R. T., Read, R. V. J Organometal. Chem. 1987, 331: 161-167; Judkins, B. D., Allen, D. G., Cook, T. A. Synth. Commun. 1996, 26(23): 4351-4367; Tommasi, R. A., Macchia, W. M., Parker, D. T. Tetrahedron. Lett. 1998, 39: 5947-5950).

The aldehyde of formula (III) as a starting material is known in some circumstances, or can be prepared according to the known methods as recited in the references (see: T. D. Harris and G. P. Roth, J. Org. Chem. 1979, 44, 146; DE 2165260, July 1972; DE 2401665, July 1974; Mijano et. al. CA 1963, 59, 13929c; E. Adler, H. D. Becker, Chem. Scand. 1961, 15, 849; E. P. Papadopoulos, M. Mardin, Ch. Issidoridis, J. Org. Chem. Soc. 1956, 78, 2543).

The compound of formula (IV) as a starting material is known, or can be prepared according to the known methods as recited in the references (see: Vorlander and Erig Justus Liebigs, Ann. Chem. 1897, 294, 314; Shriner, R. L. and Todd, H. R. Org. Synth 1943, H, 200; Frank, R. L. and Hall, H. K. Jr. J. Am. Chem. Soc. 1950, 72, 1645).

The ylene-β-ketoester compound of formula (V) or formula (VI) as a starting material can be prepared from the aldehyde of formula (III) and the compound of formula (IV) according to the known method as recited in the references (see: G. Jones, "The Knoevenagel Condensation", in Organic Reactions, Vol. XV, 204 ff. (1967)).

The compounds according to the present invention can be individually synthesized by conventional methods, or synthesized in the form of libraries (each library comprises at least two, or from 5 to 1000, more preferably from 10 to 100, of compounds) by mix-split or parallel synthesis process in combinatorial chemistry. The compounds according to the present invention can be synthesized in liquid phase or solid phase.

The process for the preparation of the compound of formula (I) is illustrated in more detail in the Examples.

The antiviral effects of the compounds according to the present invention was determined following the methods described by Sells et al. (M. A. Sells, M. L. Chen, g. Acs, Proc. Natl. Acad. Sci., 1987, 84, 1005-1009) and Korba et al., (B. E. Korba, J. L. Gerin, Antiviral Research, 1992, 19. 55-70).

The antiviral assays were carried out in 96-well microtitre plates. Only growth medium and HepG 2.2.15 cells were added to the first vertical row of the plate, as a blank control.

Stock solutions of the test compounds (50 mM) were initially dissolved in DMSO, and further dilutions were prepared in the growth medium of HepG 2.2.15 cell. The compounds according to the present invention, usually in a test concentration of 100 µg/ml ($1^{st}$ test concentration), were pipetted into each well in the second vertical test row of the microtitre plate and subsequently diluted by 2 times each time, up to $2^{10}$-fold, using the growth medium plus 2% of foetal calf serum (volume 25 p. 1).

225 µl of a HepG 2.2.15 cell suspension ($5\times10^4$ cells/ml) in the growth medium plus 2% foetal calf serum were then added to each well of the microtitre plate.

The assay mixture was incubated at 37° C., 5% $CO_2$ for 4 days. The supernatant was subsequently siphoned off and discarded, and 225 µl of freshly prepared growth medium were added to each well. Once more, the compounds according to the present invention were added, in a volume 25 µl of solution. The mixtures were incubated for another 4 days.

Before the supernatants were harvested for determining the antiviral effect, the HepG 2.2.15 cells were examined by an optical microscopy or by biochemical detecting methods (for example Alamar Blue staining or Trypan Blue staining) for cytotoxic changes.

The supernatants were subsequently harvested and siphoned onto in vacuum 96-well dot blot chambers covered with a nylon membrane (in accordance with the instructions of the manufacturer).

Determination of the Cytotoxicity

Substances-induced cytotoxic or cytostatic changes in the HepG 2.2.15 cells can be determined by for example a optical microscopy and expressed as changes in the cell morphology. Such substance-induced changes, for example, as cell lysis, vacuolization or changed cell morphology in the HepG 2.2.15 cells was apparent in comparison with those in untreated cells. The pathological changes were observed under a microscope at 8 days as indice, wherein a complete destroy being designated as 4, 75% as 3, 50% as 2, 25% as 1, and no pathological change as 0. The average degree of pathological change and inhibition percentages at various concentrations were calculated, and a half-maximum toxic concentration ($TC_{50}$) and a maximum non-toxic concentration $TC_0$ were determined according to Reed & Muench methods.

$TC_{50}$ means the concentration of the compounds according to the present invention at which 50% of the cells have a morphology which is similar to that of the corresponding cell control.

Determination of the Antiviral Activity

After transfer of the supernatants onto the nylon membrane of the blot apparatus (see above), the supernatants of the HepG 2.2.15 cells were denatured (1.5 M NaCl/0.5 M NaOH), neutralized (3 M NaI/0.5 M Tris HCl, pH 7.5) and washed (2×SSC). The DNA was subsequently baked onto the membrane By incubation of the filters at 120° C. for 2-4 hours.

Hybridization of DNA

The viral DNA of the treated HepG 2.2.15 cells on the nylon filter membrane was usually detected using non-radioactive digoxigenin-labelled hepatitis B-specific DNA probes, which were in each case labelled with digoxigenin, purified and used for hybridization in accordance with the instructions of the manufacturer.

Briefly speaking, the prehybridization and hybridization were carried out in 5×SSC, 1× a blocking agent, 0.1% N-lauroylsacosine, 0.02% SDS and 100 µg of DNA from herring sperm. The prehybridization was carried out at 60° C. for 30 minutes and the specific hybridization was carried out using 20 to 40 ng/ml of the digoxigenated denatured HBV-specific DNA (14 hours, 60° C.). The filler membrane was subsequently washed and the antibody against digoxigenin of HBV DNA was determined.

The digoxigenin-labelled DNA was detected immunologically in accordance with the instructions of the manufacturer.

Briefly speaking, the filler membranes were washed and prehybridized in the blocking agent (in accordance with the instructions of the manufacturer), and then hybridized for 30 minutes using an anti-DIG antibody previously coupled to an alkaline phosphatase. After washing, a substrate of alkaline phosphoesterase, CSPD, was added, incubated with the filter for 5 minutes, subsequently wrapped in a plastic film and incubated at 37° C. for a further 15 minutes. The chemiluminescene signals of the Hepatitis B-specific DNA were measured by exposition of the filters on an X-ray film (incubating for 10 minutes to 2 hours, depending on strength of the signals). The half-maximum inhibitory concentration ($IC_{50}$) was determined.

The half-maximum inhibitory concentration ($IC_{50}$) means the concentration of the compound according to the present invention at which the hepatitis B-specific band was reduced by 50% in comparison with an untreated sample.

The compounds according to the present invention exhibit a relatively strong anti-viral effect. Such compounds have unexpected anti-viral effect on hepatitis B (HBV), and are therefore useful for treating various virus-induced diseases, in particular those caused by acute and chronicle, persisting HBV virus infections. A chronic viral disease caused by HBV can lead to different severities of various complex symptoms. As is known, chronic hepatitis B virus infection can result in cirrhosis of liver and/or hepatocellular carcinoma.

Examples of indications for which the compounds according to the present invention can be used are:

The treatment of acute and chronic virus infections which may lead to infectious hepatitis, for example, infections by hepatitis B viruses. Particular preference is given to the treatment of chronic hepatitis B infections and the treatment of acute hepatitis B virus infection.

The pharmaceutical composition comprising the compound of the present invention can be administered by any one of following routes: oral, spray inhalation, rectal, nasal cavity, vaginal, topical, parenteral, such as subcutaneous, intravenous, intramuscular, intraperitoneally, intrathecal, intraventricular, intrasternal or intracel injection or importation, or administered by means of an explanted reservoir, preferably oral administration, intramuscular injection, intraperitoneral or intravenous administration.

The compound according to the present invention or a pharmaceutical composition comprising the compound of the present invention can be administered in unit dose form. Administration dosage form can be a liquid or solid dosage form. The liquid dosage form can be true solutions, colloids, particulates, emulsions, suspensions. Other dosage forms include, e.g., tablets, capsules, drop pills, aerosols, pills, powders, solutions, suspensions, emulsions, particulates, suppositories, lyophilized powders, clathrates, embeddings, patches, embrocations, and so on.

The pharmaceutical composition of the present invention further comprises pharmaceutically acceptable carriers, herein the pharmaceutically acceptable carriers include but are not limited to: ion exchangers, alumina, aluminum stearate, lecithin, serum protein such as human serum protein, buffers such as phosphate, glycerol, sorbic acid, potassium sorbate, partial glycerolipid mixtures of saturated vegetable fatty acids, water, salts or electrolytes, such as potamine sulfate, disodium hydrogen phosphate, potassium hydrogen phosphate, sodium chloride, zinc salts, colloidal silica, magnesium, trisilicate, polyvinylpyrrolidone, cellulose materials, polyglycol, carboxylmethylcellulose sodium, polyacrylate, beeswax, lanolin, and so on. The content of carriers in the pharmaceutical composition can be 1% to 98% by weight, generally about 80% by weight. For convenience, topical anesthetic, preservative and buffer, etc. can be directly dissolved in the carriers.

Oral tablets and capsules can contain excipients, such as binders, e.g., syrup, gum Arabic, sorbitol, bassora gum, or polyvinyl pyrrolidone, fillers, e.g., lactose, sucrose, corn starch, calcium phosphate, sorbitol, animoacetic acid, lubricants, e.g., magnesium stearate, talc, polyglycol, silica, disintegrants, e.g., potato starch, or pharmaceutically acceptable wetting agents, such as sodium lauryl sulfate. The tablets can be coated by the methods known in the field of pharmaceutics.

Oral liquids can be prepared into suspensions of water and oil, solutions, emulsions, syrups or elixirs, and can also be prepared into dried products, which are supplied with water or other suitable vehicle before use. This liquid formulation can contain routine additives, such as a suspending agent, sorbitol, cellulose methyl ether, glucose syrup, gel, hydroxyethylcellulose, carboxylmethylcellulose, aluminum stearate gel, hydrogenated edible fats, emulsifiers, such as lecithin, Span-80, Arabic gum; or non-aqueous carriers (which may contain edible oils), such as almond oil, fats, such as glycerol, ethylene glycol, or ethanol; preservatives, such as methyl p-hydroxybenzoate or propyl p-hydroxybenzoate, sorbic acid. If required, flavoring agents or coloring agents can be added.

Suppositories can contain routine suppository bases, such as cocoa butter or other glycerides.

For parenteral administration, liquid dosage forms are usually formulated from a compound and a sterile carrier. The carrier is principally selected from water. According to the difference of the carrier selected and the concentration of pharmaceutical, the compound can be dissolved into the carrier and prepared into a suspension. When an injection solution is prepared, the compound is dissolved into water, then filtrated, disinfected and packed into seal bottle or ampoule.

When administered topically to the skin, the compounds according to the present invention can be prepared into a suitable form of ointment, lotion, or cream, in which the active ingredient is suspended or dissolved into one or more carriers. The carrier for use in ointment formulation includes but is not limited to mineral oil, liquid paraffin, white paraffin, propanediol, polyethylene oxide, polyoxytrimethylene, emulsifying wax and water; the carrier for use in lotion and cream includes but is not limited to mineral oil, sorbitan monostearate, Tween-60, cetearyl ester wax, hexadecylene aromatic alcohol, 2-octyldodecanol, benzyl alcohol and water.

In the abovementioned pharmaceutical formulations, the active compounds of formula (I) should be present in a concentration of approximately from 0.1 to 99.5% by weight, preferably of approximately from 0.5 to 95% by total weight of the mixture.

The abovementioned pharmaceutical formulations may, in addition to the compounds of the formula I, comprise further pharmaceutically active compounds.

In general, it has been proved to be advantageous both in human and veterinary medicine to administer the active compound(s) in total amounts of from about 0.5 to 500 mg, preferably from 1 to 100 mg/kg of body weight per 24 hours, if appropriate in several individual doses, to obtain the desired results. An individual dose preferably contains the active compound(s) in amounts of from about 1 to 80 mg, more preferably from 1 to 30 mg/kg of body weight. However, it may be necessary to deviate from the specified dosages, depending on the species and the body weight of the subject to be treated, the nature and the severity of the disease, the formulation type and the mode of administration of the medicament, and the period or time interval of administration.

Concrete Modes for Carrying Out the Invention

Following specific examples are preferred embodiments of the present invention, and should not be construed as restriction to the present invention in any way.

The melting point of the compounds was determined by RY-1 melting point apparatus, and the thermometer was not revised. The mass spectrum of the compounds was determined by mass spectrometer Micromass ZabSpec with high resolution (a resolution of 1000). The $^1$H-NMR of the compounds was determined by means of JNM-ECA-400 superconductive NMR instrument, with operation frequency of $^1$H-NMR 400 MHz, $^{13}$C-NMR 100 MHz.

EXAMPLES

Example 1

Preparation of 2-(pyridin-3-yl)-4-(2-chloro-4-fluorophenyl)-7,7-dimethyl-4,6,7,8-tetrahydroquinazolin-5(1H)-one

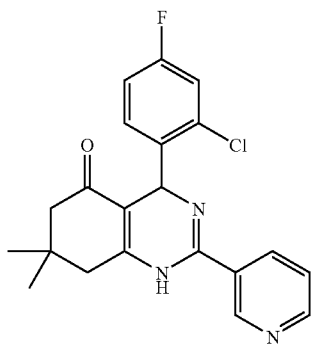

3-Pyridinecarboxamidine hydrochloride (Schaefer F. C., Peters G. A., et al. J. Org. Chem.; 1961; 26(2); 412-418.) 2.164 mmol, 2-chloro-4-fluorobenzaldehyde 2.164 mmol, 5,5-dimethyl-1,3-cyclohexanedione 2.164 mmol and sodium acetate 3.2 mmol were reacted in 8 ml of anhydrous ethanol under refluxing for 18 hr, condensed, and ethyl acetate and water and 1N HCl were added to separate the layers. The water layer was adjusted with concentrated NaOH solution until the pH to be basic, then ethyl acetate was added and extracted twice. The organic layers were combined, dried over anhydrous sodium sulfate and separated by column chromatography to obtain a yellow solid of 0.22 g (yield 26%); mp 186-187° C. $^1$H-NMR (400 MHz, CDCl$_3$) δ 1.15 (3H, s, CH$_3$); 1.16 (3H, s, CH$_3$); 2.31 (2H, s, CH$_2$); 2.53-2.69 (2H, m, CH$_2$); 6.07 (1H, s, CH); 6.94-6.96 (1H, m, ArH); 7.14-7.17 (1H, m, ArH); 7.23-7.26 (1H, m, ArH); 7.34-7.38 (1H, m, ArH) 8.07-8.09 (1H, m, ArH); 8.69-8.71 (1H, m, ArH); 8.89 (1H, m, ArH). MS (EI) 383.1 (M$^+$).

Example 2

Preparation of 2-(pyridin-3-yl)-4-(2-chloro-4-fluorophenyl)-7,7-dimethyl-4,6,7,8-tetrahydroquinazolin-5(1H)-one hydrochloride

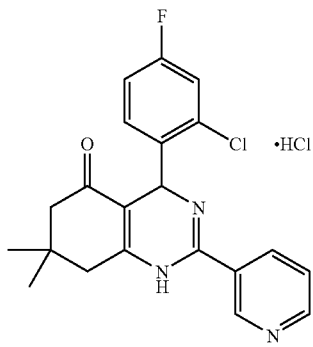

0.38 g of the object compound obtained in Example 1 was dissolved in 2 ml anhydrous ethanol, to which hydrogen chloride ethyl solution was added dropwise to precipitate a solid, and filtered to obtain an off-white powdery solid 0.41 g, mp 197-199° C. The solid was very easily soluable in water, soluble slightly in methanol and ethanol, and insoluble in dichloromethane, ethyl acetate, acetone, etc.

Example 3

Preparation of 2-(pyridin-3-yl)-4-(2-chloro-4-fluorophenyl)-4,6,7,8-tetrahydroquinazolin-5(1H)-one

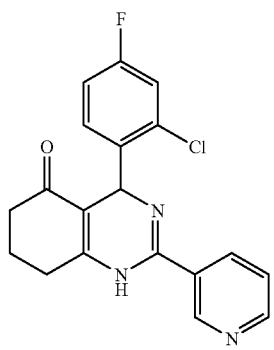

3-pyridinecarboxamidine hydrochloride (Schaefer F. C., Peters G. A., et al. J. Org. Chem.; 1961; 26(2); 412-418.) 2.164 mmol, 2-chloro-4-fluorobenzaldehyde 2.164 mmol, 1,3-cyclohexanedione 2.164 mmol and sodium acetate 3.2 mmol were reacted in 8 ml of anhydrous ethanol under refluxing for 18 hr, condensed, to which ethyl acetate, water and 1N HCl were added and then the layers were separated. The water layer was adjusted with concentrated NaOH solution until the pH to be basic, then ethyl acetate was added and extracted twice. The organic layers were combined, dried over anhydrous sodium sulfate and separated by column chromatography to obtain a yellow solid of 0.21 g (yield 27%); $^1$H-NMR (400 MHz, CDCl$_3$) δ 2.13-2.17 (2H, m, CH$_2$); 2.43-2.51 (2H, m, CH$_2$); 2.63-2.83 (2H, m, CH$_2$); 6.06 (1H, s, CH); 7.15-7.22 (2H, m, ArH); 7.34-7.38 (1H, m, ArH); 8.07-8.09 (1H, m, ArH); 8.70-8.71 (1H, m, ArH); 8.89 (1H, m, ArH). MS (HREI) 355.0887 (M$^+$).

Example 4

Preparation of 2-(pyridin-3-yl)-4-(4-fluorophenyl)-7,7-dimethyl-4,6,7,8-tetrahydroquinazolin-5(1H)-one

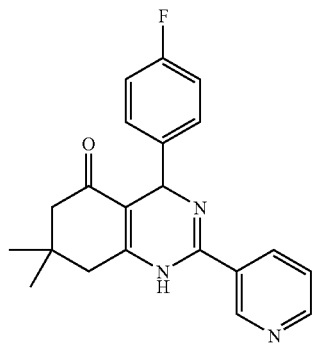

The method of Example 1 was used, wherein 2-chloro-4-fluorobenzaldehyde was replaced by 4-fluorobenzaldehyde, to obtain a light yellow granule of 0.23 g (yield 30%). ¹H-NMR (400 MHz, CDCl₃) 1.02 (3H, s, CH₃); 1.11 (3H, s, CH₃); 2.18-2.29 (2H, m, CH₂); 2.48-2.59 (2H, m, CH₂); 5.70 (1H, s, CH); 6.96-7.00 (2H, m, ArH); 7.34-7.48 (3H, m, ArH); 8.15-8.17 (1H, m, ArH) 8.68-8.70 (1H, m, ArH); 8.95 (1H, m, ArH); MS (EI) 349.2 (M⁺).

Example 5

Preparation of 2-(pyridin-3-yl)-4-phenyl-7,7-dimethyl-4,6,7,8-tetrahydroquinazolin-5(1H)-one

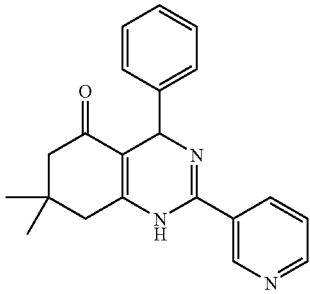

The method of Example 1 was used, wherein 2-chloro-4-fluorobenzaldehyde was replaced by benzaldehyde to obtain a light yellow granule of 0.20 g (yield 28%). ¹H-NMR (400 MHz, CDCl₃) 1.01 (3H, s, CH₃); 1.10 (3H, s, CH₃); 2.17-2.27 (2H, m, CH₂); 2.50-2.53 (2H, m, CH₂); 5.70 (1H, s, CH); 7.24-7.38 (6H, m, ArH); 8.13-8.15 (1H, m, ArH); 8.67-8.68 (1H, m, ArH); 8.94-8.95 (1H, m, ArH); MS (EI) 331.2 (M⁺).

Example 6

Preparation of 2-(pyridin-3-yl)-4-phenyl-4,6,7,8-tetrahydroquinazolin-5(1H)-one

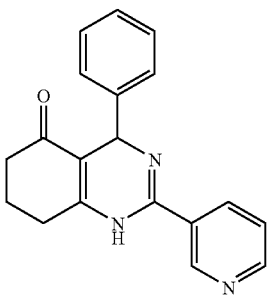

The method of Example 3 was used, wherein 2-chloro-4-fluorobenzaldehyde was replaced by benzaldehyde to obtain a light yellow granules of 0.21 g (yield 31%). ¹H-NMR (400 MHz, CDCl₃) 1.01 (3H, s, CH₃); 1.10 (3H, s, CH₃); 2.17-2.27 (2H, m, CH₂); 2.50-2.53 (2H, m, CH₂); 5.70 (1H, s, CH); 7.24-7.38 (6H, m, ArH); 8.13-8.15 (1H, m, ArH); 8.67-8.68 (1H, m, ArH); 8.94-8.95 (1H, m, ArH). MS (EI) 331.2 (M⁺).

Example 7

Preparation of 2-(pyridin-3-yl)-4-(2-chlorophenyl)-7,7-dimethyl-4,6,7,8-tetrahydroquinazolin-5(1H)-one

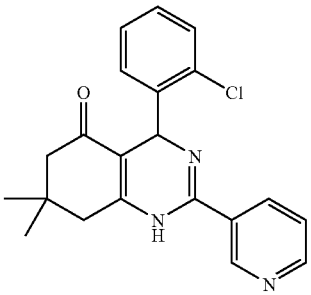

The method of Example 1 was used, wherein 2-chloro-4-fluorobenzaldehyde was replaced by 2-chlorobenzaldehyde to obtain a light yellow solid 0.22 g (yield 26%); ¹H-NMR (400 MHz, CDCl₃) δ 1.15 (3H, s, CH₃); 1.18 (3H, s, CH₃); 2.32 (2H, s, CH₂); 2.54-2.72 (2H, m, CH₂); 6.11 (1H, s, CH); 6.88 (1H, s, NH); 7.21-7.26 (3H, m, ArH); 7.32-7.39 (2H, m, ArH); 8.06-8.08 (1H, m, ArH); 8.69-8.70 (1H, m, ArH); 8.88-8.89 (1H, m, ArH). MS (EI) 365.2 (M⁺).

Example 8

2-(pyridin-3-yl)-4-(4-fluorophenyl)-4,6,7,8-tetrahydroquinazolin-5(1H)-one

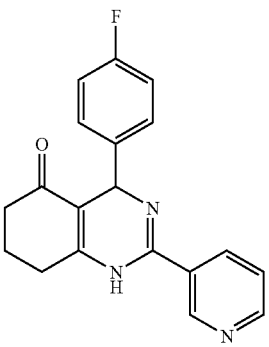

The method of Example 3 was used, wherein 2-chloro-4-fluorobenzaldehyde was replaced by 4-fluorobenzaldehyde to obtain a light yellow granule of 0.19 g (yield 27%); ¹H-NMR (400 MHz, CDCl₃) δ 2.00 (2H, m, CH₂); 2.30-2.40 (2H, m, CH₂); 2.50-2.67 (2H, m, CH₂); 5.71 (1H, s, CH); 6.96-7.00 (2H, m, ArH); 7.32-7.40 (3H, m, ArH); 8.13-8.16 (1H, m, ArH); 8.69-8.70 (1H, m, ArH); 8.95-8.96 (1H, m, ArH). MS (HREI) 321.1277 (M⁺).

Example 9

2-(pyridin-3-yl)-4-(2-chlorophenyl)-4,6,7,8-tetrahydroquinazolin-5(1H)-one

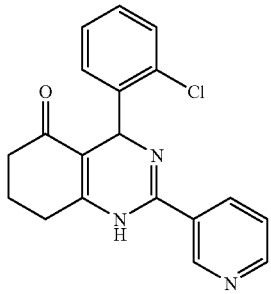

The method of Example 3 was used, wherein 2-chloro-4-fluorobenzaldehyde was replaced by 2-chlorobenzaldehyde to obtain a light yellow solid 0.16 g (yield 24%); $^1$H-NMR (400 MHz, CDCl$_3$) δ 2.12-2.18 (2H, m, CH$_2$); 2.54 (2H, m, CH$_2$); 2.63-2.85 (2H, m, CH$_2$); 6.10 (1H, s, CH); 7.21-7.26 (3H, m, ArH); 7.33-7.42 (2H, m, ArH); 8.06-8.08 (1H, m, ArH); 8.68-8.69 (1H, m, ArH); 8.88-8.89 (1H, m, ArH). MS (HREI) 337.0983 (M$^+$).

Example 10

2-(2,4,6-trifluorophenyl)-4-(2-chloro-4-fluorophenyl)-4,6,7,8-tetrahydroquinazolin-5(1H)-one

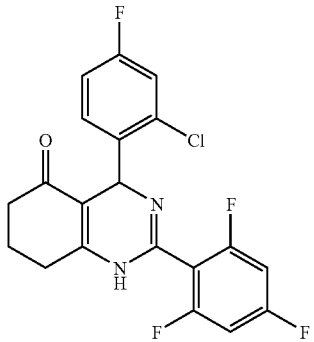

The method of Example 3 was used, wherein 3-pyridinecarboxamidine hydrochloride was replaced by 2,4,6-trifluorobenzamidine acetate to obtain a off-white solid of 0.22 g (yield 25%); $^1$H-NMR (400 MHz, DMSO-d$_6$) δ 1.93-1.95 (2H, m, CH$_2$); 2.15-2.32 (2H, m, CH$_2$); 5.87 (1H, s, CH); 7.11-7.16 (1H, m, ArH); 7.24-7.28 (1H, m, ArH); 7.30-7.39 (5H, m, ArH); 10.09 (1H, s, NH). MS (EI) 408.0 (M$^+$).

Example 11

2-(2,4,6-trifluorophenyl)-4-(2-chloro-4-fluorophenyl)-7,7-dimethyl-4,6,7,8-tetrahydroquinazolin-5(1H)-one

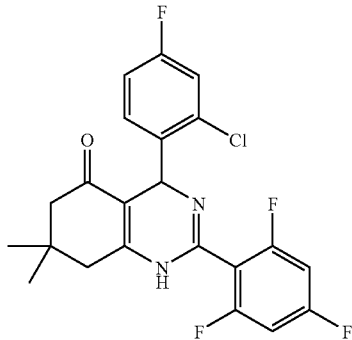

The method of Example 1 was used, wherein 3-pyridinecarboxamidine hydrochloride was replaced by 2,4,6-trifluorobenzamidine acetate to obtain a off-white solid of 0.2 g (yield 22%); $^1$H-NMR (400 MHz, DMSO-d$_6$) δ 1.03 (3H, s, CH$_3$); 1.05 (3H, s, CH$_3$); 2.04-2.43 (4H, m, CH$_2$); 5.91 (1H, s, CH); 7.19-7.39 (5H, m, ArH); 10.08 (1H, s, NH). MS (EI) 436.0 (M$^+$).

Example 12

2-(pyridin-2-yl)-4-(2-chloro-4-fluorophenyl)-7,7-dimethyl-4,6,7,8-tetrahydroquinazolin-5(1H)-one

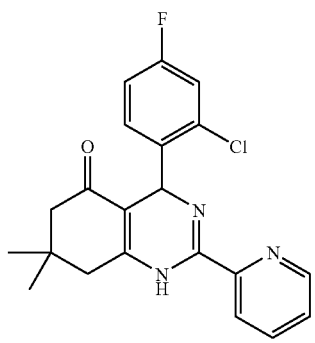

The method of Example 1 was used, wherein 3-pyridinecarboxamidine hydrochloride was replaced by 2-pyridinecarboxamidine hydrochloride to obtain a yellow solid of 0.22 g (yield 26%); $^1$H-NMR (400 MHz, CDCl$_3$) δ 1.15 (3H, s, CH$_3$); 1.16 (3H, s, CH$_3$); 2.31 (2H, s, CH$_2$); 2.48-2.72 m, CH$_2$); 6.15 (1H, s, CH); 6.89-6.92 (1H, m, ArH); 7.11-7.13 (1H, m, ArH); 8.16-8.72 (2H, m, ArH). MS (HREI) 383.1202 (M$^+$).

Example 13

2-(pyrazin-2-yl)-4-(2-chloro-4-fluorophenyl)-7,7-dimethyl-4,6,7,8-tetrahydroquinazolin-5(1H)-one

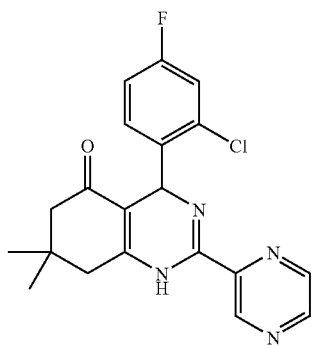

The method of Example 1 was used, wherein 3-pyridinecarboxamidine hydrochloride was replaced by 2-amidinopyrazinium hydrochloride to obtain a yellow solid of 0.28 g (yield 34%); $^1$H-NMR (400 MHz, CDCl$_3$) δ 1.15 (3H, s, CH$_3$); 1.17 (3H, s, CH$_3$); 2.32 (2H, s, CH$_2$); 2.48-2.70 (2H, m, CH$_2$); 6.15-6.19 (1H, m, CH); 6.90-6.92 (1H, m, ArH); 7.12-7.30 (1H, m, ArH); 8.11 (H, s, ArH); 8.50 (H, s, ArH); 8.70 (2H, m, ArH); 9.57 (1H, s, NH). MS (HREI) 384.3 (M$^+$).

Example 14

2-(pyrazin-2-yl)-4-(2-chlorophenyl)-7,7-dimethyl-4,6,7,8-tetrahydroquinazolin-5(1H)-one

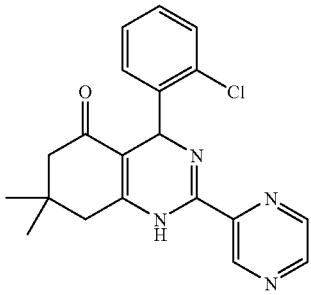

The method of Example 1 was used, wherein 3-pyridinecarboxamidine hydrochloride and 2-chloro-4-fluorobenzaldehyde were separately replaced by 2-amidinopyrazinium hydrochloride and 2-chlorobenzaldehyde to obtain a yellow solid of 0.26 g (yield 33%); $^1$H-NMR (400 MHz, CDCl$_3$) δ 1.12-1.19 (6H, m, CH$_3$); 2.33 (2H, s, CH$_2$); 2.48-2.72 (2H, m, CH$_2$); 6.19 (1H, s, CH); 7.14-7.40 (4H, m, ArH); 8.17 (1H, s, ArH); 8.50 (1H, m, ArH); 8.70 (1H, m, ArH); 9.57 (1H, s, NH). MS (EI) 366.3 (M$^+$).

Example 15

2-(pyrazin-2-yl)-4-(2-chloro-4-fluorophenyl)-4,6,7,8-tetrahydroquinazolin-5(1H)-one

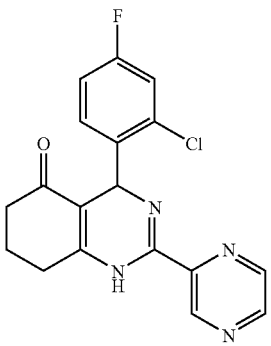

The method of Example 3 was used, wherein 3-pyridinecarboxamidine hydrochloride was replaced by 2-amidinopyrazinium hydrochloride to obtain a yellow solid of 0.27 g (yield 35%); $^1$H-NMR (400 MHz, CDCl$_3$) δ 2.14-2.19 (2H, m, CH$_2$); 2.47 (2H, s, CH$_2$); 2.72-2.87 (2H, m, CH$_2$); 6.14-6.23 (1H, m, CH); 6.91-6.95 (1H, m, ArH); 7.13-7.26 (2H, m, ArH); 8.21-8.52 (2H, m, ArH); 8.71 (1H, m, ArH); 9.58 (1H, s, NH). MS (EI) 356.2 (M$^+$).

Example 16

2-(pyrazin-2-yl)-4-(2-chlorophenyl)-4,6,7,8-tetrahydroquinazolin-5(1H)-one

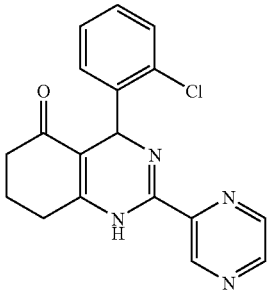

The method of Example 3 was used, wherein 3-pyridinecarboxamidine hydrochloride and 2-chloro-4-fluorobenzaldehyde were separately replaced by 2-amidinopyrazinium hydrochloride and 2-chlorobenzaldehyde to obtain a yellow solid of 0.21 g (yield 29%); $^1$H-NMR (400 MHz, CDCl$_3$) δ 2.15-2.19 (2H, m, CH$_2$); 2.45-2.85 (4H, s, CH$_2$); 6.19 (1H, s, CH); 7.13-7.40 (4H, m, ArH); 8.27 (1H, s, ArH); 8.51 (H, m, ArH); 8.69 (H, m, ArH); 9.57 (1H, s, NH). MS (EI) 338.2 (M$^+$).

Example 17

2-(3-fluoropyridin-2-yl)-4-(2-chloro-4-fluorophenyl)-7,7-dimethyl-4,6,7,8-tetrahydroquinazolin-5(1H)-one

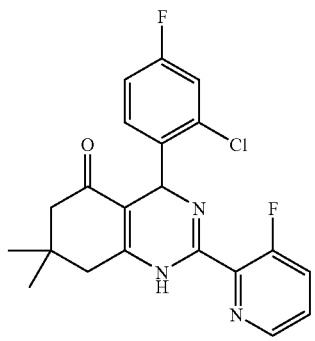

The method of Example 1 was used, wherein 3-pyridinecarboxamidine hydrochloride was replaced by 3-fluoropyridin-2-carboxamidine hydrochloride to obtain a yellow solid of 0.26 g (yield 30%); $^1$H-NMR (400 MHz, CDCl$_3$) δ 1.15 (3H, s, CH$_3$); 1.16 (3H, s, CH$_3$); 2.25-2.35 (2H, m, CH$_2$); 2.53-2.57 (2H, m, CH$_2$); 6.19 (1H, s, CH); 6.91-6.93 (1H, m, ArH); 7.11-7.14 (1H, m, ArH); 7.29-7.33 (1H, s, ArH); 7.43-7.46 (1H, m, ArH); 7.51-7.56 (1H, m, ArH); 8.39-8.40 (1H, m, ArH). MS (EI) 401.1 (M$^+$).

Example 18

2-(3-fluoropyridin-2-yl)-4-(2-chloro-4-fluorophenyl)-4,6,7,8-tetrahydroquinazolin-5(1H)-one

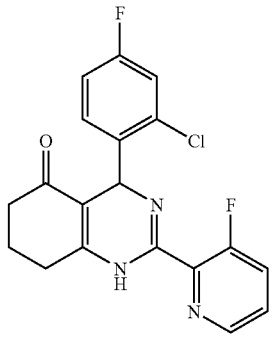

The method of Example 3 was used, wherein 3-pyridinecarboxamidine hydrochloride was replaced by 3-fluoropyridin-2-carboxamidine hydrochloride to obtain a yellow solid of 0.25 g (yield 35%); $^1$H-NMR (400 MHz, CDCl$_3$) δ 2.11-2.17 (2H, m, CH$_2$); 2.39-2.50 (3H, s, CH$_3$); 2.64-2.78 (2H, m, CH$_2$); 6.18 (1H, s, CH); 6.89-6.93 (1H, m, ArH); 7.12-7.14 (1H, m, ArH); 7.24-7.28 (1H, m, ArH); 7.42-7.46 (1H, m, ArH); 8.39-8.40 (1H, m, ArH). MS (EI) 373.1 (M$^+$).

Example 19

2-(furan-2-yl)-4-(2-chloro-4-fluorophenyl)-7,7-dimethyl-4,6,7,8-tetrahydroquinazolin-5(1H)-one

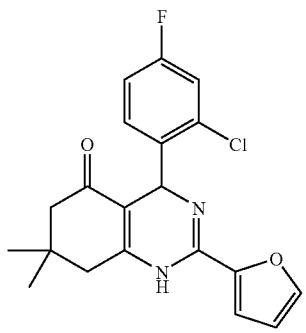

The method of Example 1 was used, wherein 3-pyridinecarboxamidine hydrochloride was replaced by furan-2-carboxamidine hydrochloride to obtain a light yellow solid 0.24 g (yield 30%); $^1$H-NMR (400 MHz, CDCl$_3$) δ 1.13 (3H, s, CH$_3$); 1.15 (3H, s, CH$_3$); 2.29 (2H, m, CH$_2$); 2.50-2.63 (2H, m, CH$_2$); 6.05 (1H, s, CH); 6.53-6.54 (1H, m, ArH); 6.92-6.93 (1H, m, ArH); 6.89-6.96 (1H, m, ArH); 7.19-7.21 (3H, m, ArH); 7.50 (1H, m, ArH). MS (EI) 372.1 (M$^+$).

Example 20

2-(furan-2-yl)-4-(2-chloro-4-fluorophenyl)-4,6,7,8-tetrahydroquinazolin-5(1H)-one

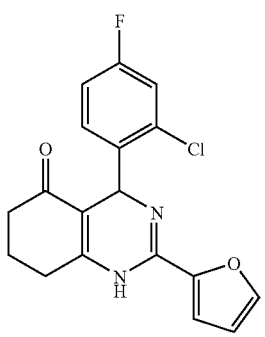

The method of Example 3 was used, wherein 3-pyridinecarboxamidine hydrochloride was replaced by furan-2-carboxamidine hydrochloride to obtain a light yellow solid 0.21 g (yield 28%); $^1$H-NMR (400 MHz, CDCl$_3$) δ 2.12-2.16 (2H, m, CH$_2$); 2.42-2.46 (2H, m, CH$_2$); 2.59-2.67 (2H, m, CH$_2$); 6.03 (1H, s, CH); 6.52-6.53 (1H, m, ArH); 6.89-6.96 (1H, m, ArH); 7.19-7.21 (3H, m, ArH); 7.19-7.21 (3H, m, ArH); 7.50 (1H, m, ArH). MS (EI) 344.1 (M$^+$).

Example 21

2-(pyridin-2-yl)-4-(2-chloro-4-fluorophenyl)-4,6,7,8-tetrahydroquinazolin-5(1H)-one

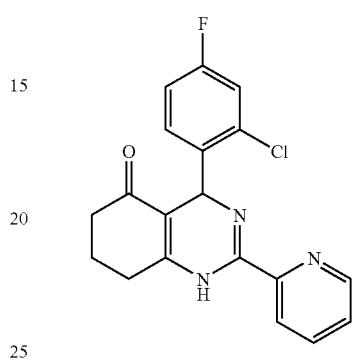

The method of Example 3 was used, wherein 3-pyridinecarboxamidine hydrochloride was replaced by 2-pyridinecarboxamidine hydrochloride to obtain a light yellow solid 0.24 g (yield 31%); $^1$H-NMR (400 MHz, CDCl$_3$) δ 2.13-2.15 (2H, m, CH$_2$); 2.45 (2H, s, CH$_2$); 2.65-2.85 (2H, m, CH$_2$); 6.14-6.22 (1H, m, CH); 6.90-9.92 (1H, m, ArH); 7.16-7.26 (1H, m, ArH); 8.19-8.54 (2H, m, ArH); 8.77 (1H, s, NH). MS (EI) 355.2 (M$^+$).

Example 22

2-(pyridin-2-yl)-4-(2-chlorophenyl)-4,6,7,8-tetrahydroquinazolin-5(1H)-one

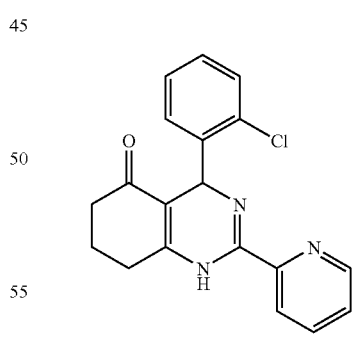

The method of Example 3 was used, wherein 3-pyridinecarboxamidine hydrochloride and 2-chloro-4-fluorobenzaldehyde were separately replaced by 2-pyridinecarboxamidine hydrochloride and 2-chlorobenzaldehyde to obtain a light yellow solid 0.21 g (yield 29%); $^1$H-NMR (400 MHz, CDCl$_3$) δ 2.13-2.17 (2H, m, CH$_2$); 2.44-2.47 (2H, m, CH$_2$); 2.65-2.86 (2H, m, CH$_2$); 6.19-6.28 (1H, BR, CH); 7.17-7.39

(5H, m, ArH); 7.77-7.80 (1H, m, ArH); 8.20-8.59 (2H, m, ArH); 8.76 (1H, s, NH). MS (EI) 337.1 (M+).

Example 23

2-(pyridin-2-yl)-4-(4-fluorophenyl)-4,6,7,8-tetrahydroquinazolin-5(1H)-one

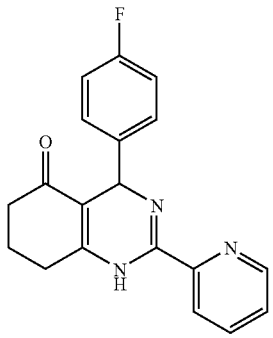

The method of Example 3 was used, wherein 3-pyridinecarboxamidine hydrochloride and 2-chloro-4-fluorobenzaldehyde were separately replaced by 2-pyridinecarboxamidine hydrochloride and 4-fluorobenzaldehyde to obtain a light yellow solid 0.23 g (yield 33%); $^1$H-NMR (400 MHz, CDCl$_3$) δ 2.04-2.07 (2H, m, CH$_2$); 2.35-2.47 (2H, m, CH$_2$); 2.61-2.71 (2H, m, CH$_2$); 5.79-5.92 (1H, BR, CH); 6.94-6.98 (2H, m, ArH); 7.34-7.44 (3H, m, ArH); 7.83 (1H, m, ArH); 8.33-8.56 (2H, m, ArH); 8.79 (1H, s, NH). MS (EI) 321.2 (M+).

Example 24

2-(pyridin-2-yl)-4-phenyl-4,6,7,8-tetrahydroquinazolin-5(1H)-one

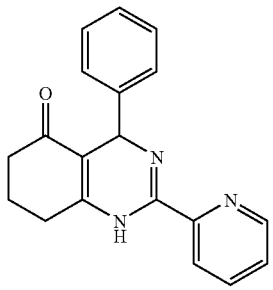

The method of Example 3 was used, wherein 3-pyridinecarboxamidine hydrochloride and 2-chloro-4-fluorobenzaldehyde were separately replaced by 2-pyridinecarboxamidine hydrochloride and benzaldehyde to obtain a light yellow solid 0.19 g (yield 30%); $^1$H-NMR (400 MHz, CDCl$_3$) δ 2.04-2.05 (2H, m, CH$_2$); 2.34-2.76 (4H, m, CH$_2$); 5.79-5.97 (1H, BR, CH); 7.21-7.30 (3H, m, ArH); 7.39-7.43 (3H, m, ArH); 7.83 (1H, m, ArH); 8.34-8.42 (1H, m, ArH); 8.54-8.55 (1H, m, ArH); 8.78 (1H, s, NH). MS (EI) 303.2 (M+).

Example 25

2-(thiazol-2-yl)-4-(2-chloro-4-fluorophenyl)-7,7-dimethyl-7,8-dihydroquinazolin-5(1H)-one

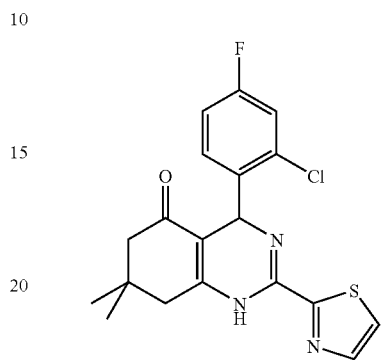

2-thiazolecarboxamidine hydrochloride (Schaefer F. C., Peters G. A., et al.) 2.164 mmol, 2-chloro-4-fluorobenzaldehyde 2.164 mmol, 5,5-dimethyl-1,3-cyclohexanedione 2.164 mmol and sodium acetate 3.2 mmol were reacted in 8 ml of anhydrous ethanol under refluxing for 18 hr, condensed, to which ethyl acetate and water and 1N HCl were added, and separated. The water layer was adjusted with concentrated NaOH solution until pH value to be basic, then ethyl acetate was added and extracted twice. The organic layers were combined, dried over anhydrous sodium sulfate, and separated by column chromatography to obtain a yellow crystal 0.23 g (yield 28%); $^1$H-NMR (400 MHz, CDCl$_3$-d$_1$) δ 7.95-7.85 (m, 1H, ArH); 7.64-7.47 (m, 1H, ArH); 7, 34-7.24 (m, 1H, ArH); 7.13-7.11 (m, 1H, ArH); 6.11 (s, 1H, CH); 2.70-2.52 (m, 2H, CH$_2$); 2.43-2.26 (m, 2H, CH$_2$); 1.15 (s, 6H, CH$_3$). HREI: 389.0765 (M+).

Example 26

2-(thiazol-2-yl)-4-(2-chloro-4-fluorophenyl)-7,8-dihydroquinazolin-5(1H)-one

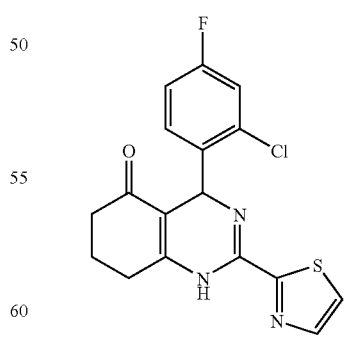

2-thiazolecarboxamidine hydrochloride (Schaefer P. C., Peters G. A., et al.) 2.164 mmol, 2-chloro-4-fluorobenzaldehyde 2.164 mmol, 1,3-cyclohexanedione 2.164 mmol and sodium acetate 3.2 mmol were reacted in 8 ml anhydrous ethanol under refluxing for 18 hr, and condensed, to which ethyl acetate and water and 1N HCl were added and the layers were separated. The water layer was adjusted with concentrated NaOH solution until pH value to be basic, then ethyl acetate was added again and extracted twice. The organic layers were combined, dried over anhydrous sodium sulfate, and separated by column chromatography to obtain a yellow crystal of 0.21 g (yield 27%); $^1$H-NMR (400 MHz, CDCl$_3$-d$_1$) δ 7.86 (m, 1H, ArH); 7.73-7.52 (m, 1H, ArH); 7.24-7.21 (m, 1H, ArH); 7.15-7.12 (m, 1H, ArH); 6.94-6.92 (m, 1H, ArH); 6.11 (s, 1H, CH); 2.80-2.47 (m, 2H, CH$_2$); 2.14-2.11 (m, 2H, CH$_2$). HREI: 361.0450 (M$^+$).

Example 27

2-(thiazol-2-yl)-4-(4-fluorophenyl)-7,8-dihydro-quinazolin-5(1H)-one

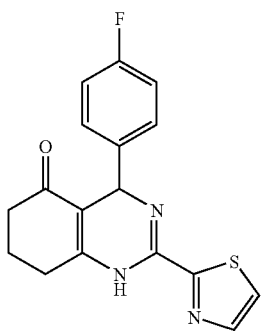

The method of Example 26 was used, wherein 2-chloro-4-fluorobenzaldehyde was replaced by 4-fluorobenzaldehyde to obtain a light yellow granule of 0.20 g (yield 30%). $^1$H-NMR (400 MHz, CDCl$_3$-d$_1$) δ 8.1-8.0 (s, 1H, NH); 7.87-7.86 (m, 1H, ArH); 7.59-7.52 (s, 1H, ArH); 7.39-7.34 (m, 2H, ArH); 7.00-6.95 (m, 1H, ArH); 5.88-5.72 (d, 1H, CH); 2.59-2.38 (m, 4H, CH$_2$); 2.07-2.05 (m, 2H, CH$_2$). HREI: 327.0840 (M$^+$).

Example 28

2-(thiazol-2-yl)-4-(2-chlorophenyl)-7,8-dihydro-quinazolin-5(1H)-one

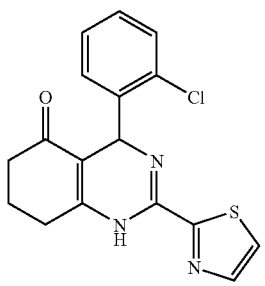

The method of Example 26 was used, wherein 2-chloro-4-fluorobenzaldehyde was replaced by 2-chlorobenzaldehyde to obtain a light yellow granule of 0.22 g (yield 32%). $^1$H-NMR (400 MHz, CDCl$_3$-d$_1$) δ 7.85 (s, 1H, ArH); 7.69 (s, 1H, NH); 7.53 (s, 1H, ArH); 7.39-7.37 (m, 1H, ArH); 7.20 (m, 3H, ArH); 6.15 (s, 1H, CH); 2.80-2.62 (m, 2H, CH$_2$); 2.46-2.43 (m, 2H, CH$_2$); 2.16-2.10 (m, 2H, CH$_2$). HREI: 343.0547 (M$^+$).

Example 29

2-(thiazol-2-yl)-4-(2-chloro-4-fluorophenyl)-7,7-dimethyl-7,8-dihydroquinazolin-5(1H)-one

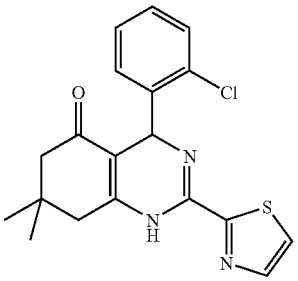

The method of Example 25 was used, wherein 2-chloro-4-fluorobenzaldehyde was replaced by 2-chlorobenzaldehyde to obtain a light yellow granule of 0.24 g (yield 31%). $^1$H-NMR (400 MHz, CDCl$_3$-d$_1$) δ 7.85 (s, 1H, ArH), 7.69 (s, 1H, NH), 7.55 (s, 1H, ArH), 7.39-7.37 (m, 1H, ArH), 7.27-7.26 (m, 1H, ArH); 7.21-7.19 (m, 2H, ArH); 6.16 (s, 1H, CH); 2.72-2.53 (m, 2H, CH$_2$); 2.31 (m, 2H, CH$_2$); 1.14 (s, 3H, CH$_3$); 1.12 (s, 3H, CH$_3$). HREI: 371.0862 (M$^+$).

Example 30

2-(pyridin-4-yl)-4-(2-chloro-4-fluorophenyl)-7,7-dimethyl-7,8-dihydroquinazolin-5(1H)-one

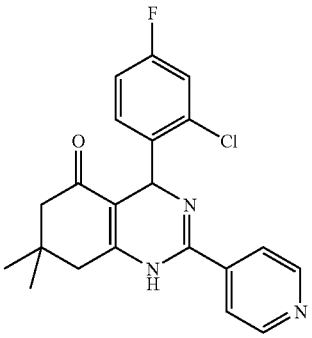

The method of Example 25 was used, wherein 2-thiazole-carboxamidine hydrochloride was replaced by 4-pyridinecarboxamidine hydrochloride to obtain a light yellow granule of 0.27 g (yield 33%). $^1$H-NMR (400 MHz, CDCl$_3$-d$_1$) δ 8.70-8.69 (d, 2H, J=5.6 Hz, ArH); 7.59-7.58 (d, 2H, J=4.4 Hz, ArH); 7.26-7.24 (m, 1H, ArH); 7.17-7.14 (d, 1H, J$_1$=2.4 Hz, J$_2$=8.0 Hz, ArH); 6.98-6.94 (t, 1H, J$_1$=2.4 Hz, J$_2$=8.0 Hz, ArH); 6.08 (s, 1H, CH); 2.64-2.52 (m, 2H, CH$_2$); 2.31 (s, 2H, CH$_2$); 1.16 (s, 3H, CH$_3$); 1.15 (s, 3H, CH$_3$). HREI: 383.1201 (M$^+$).

Example 31

2-(pyridin-4-yl)-4-(2-chloro-4-fluorophenyl)-7,8-dihydroquinazolin-(1H)-one

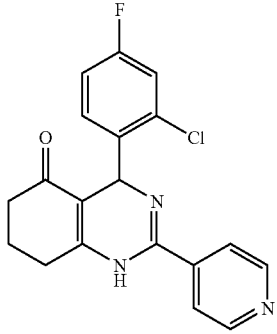

The method of Example 26 was used, wherein 2-thiazole-carboxamidine hydrochloride was replaced by 4-pyridinecarboxamidine hydrochloride to obtain a light yellow granule of 0.34 g (yield 36%). $^1$H-NMR (400 MHz, CDCl$_3$-d$_1$) δ 8.70-8.65 (d, 2H, J=6.0 Hz, ArH); 7.59-7.57 (d, 2H, J=6.0 Hz, ArH); 7.26-7.15 (m, 2H, ArH); 6.95 (m, 1H, ArH); 6.06-6.04 (s, 1H, ArH); 2.68-2.43 (m, 4H, CH$_2$); HREI: 355.0891 (M$^+$).

Example 32

2-(3,5-difluoropyridin-2-yl)-4-(2-chloro-4-fluorophenyl)-7,7-dimethyl-7,8-dihydroquinazolin-5(1H)-one

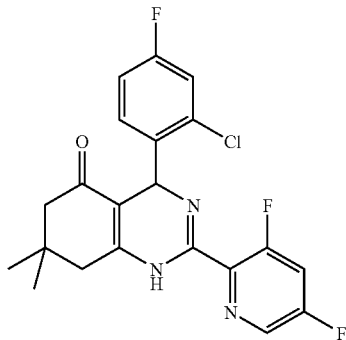

The method of Example 25 was used, wherein 2-thiazole-carboxamidine hydrochloride was replaced by 3,5-difluoropyridin-2-carboxamidine hydrochloride to obtain a light yellow granule of 0.18 g (yield 20%). $^1$H-NMR (400 MHz, CDCl$_3$-d$_1$) δ 8.30-8.29 (m, 1H, ArH); 8.05 (s, 1H, NH); 7.32-7.29 (t, 1H, J$_1$=2.4 Hz, J$_2$=8.0 Hz, ArH); 7.29-7.26 (m, 1H, ArH); 7.14-7.11 (d, 1H, J$_1$=2.4 Hz, J$_2$=8.0 Hz, ArH); 6.94-6.90 (t, 1H, J$_1$=2.4 Hz, J$_2$=8.0 Hz, ArH); 6.16 (s, 1H, CH); 2.70-2.53 (m, 2H, CH$_2$); 2.30 (m, 4H, CH$_2$); 1.16 (s, 3H, CH$_3$); 1.15 (s, 3H, CH$_3$). HREI: 419.1010 (M$^+$).

Example 33

2-(3,5-difluoropyridin-2-yl)-4-(2-chloro-4-fluorophenyl)-7,8-dihydroquinazolin-5(1H)-one

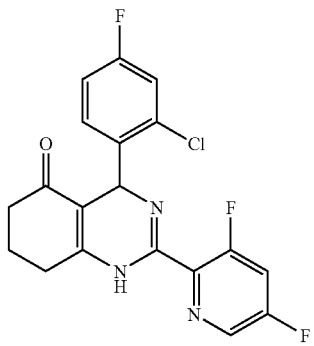

The method of Example 26 was used, wherein 2-thiazole-carboxamidine hydrochloride was replaced by 3,5-difluoropyridin-2-carboxamidine hydrochloride to obtain a light yellow granule of 0.20 g (yield 24%). $^1$H-NMR (400 MHz, CDCl$_3$-d$_1$) δ 8.30 (m, 1H, ArH); 7.35-7.30 (t, 1H, J$_1$=2.4 Hz, J$_2$=8.0 Hz, ArH); 7.26-7.22 (m, 1H, ArH); 7.15-7.12 (dd, 1H, J$_1$=2.4 Hz, J$_2$=8.0 Hz, ArH); 6.94-6.89 (t, 1H, J$_1$=2.4 Hz, J$_2$=8.0 Hz, ArH); 6.15-6.14 (s, 1H, CH); 2.80-2.69 (m, 2H, CH$_2$); 2.48-2.43 (m, 2H, CH$_2$); 2.16-2.13 (m, 2H, CH$_2$). HREI: 391.0695 (M$^+$).

Example 34

2-(3-fluoropyridin-2-yl)-4-(4-fluorophenyl)-7,7-dimethyl-7,8-dihydroquinazolin-5(1H)-one

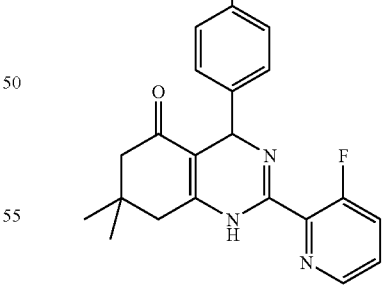

The method of Example 25 was used, wherein 2-thiazole-carboxamidine hydrochloride was replaced by 3-fluoropyridin-2-carboxamidine hydrochloride, and 2-chloro-4-fluorobenzaldehyde was replaced by 4-fluorobenzaldehyde to obtain a light yellow granule of 0.24 g (yield 30%). $^1$H-NMR (400 MHz, CDCl$_3$-d$_1$) δ 8.41-8.40 (m, 1H, ArH); 7.60-7.55 (m, 1H, ArH); 7.49-7.42 (m, 1H, ArH); 7.42-7.38 (t, 2H, J=8.4 Hz, ArH); 6.99-6.94 (t, 2H, J=9, 2 Hz, ArH); 5.91 (s, 1H, CH), 2.50 (s, 2H, CH$_2$); 2.33-2.23 (m, 2H, CH$_2$); 1.12 (s, 3H, CH$_3$); 1.04 (s, 3H, CH$_3$). HREI: 367.1498 (M$^+$).

Example 35

2-(3-fluoropyridin-2-yl)-4-(4-fluorophenyl)-7,8-dihydroquinazolin-5(1H)-one

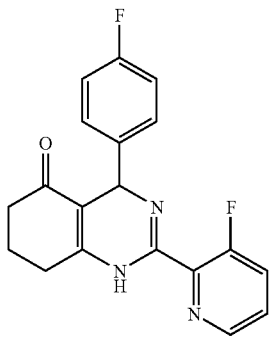

The method of Example 26 was used, wherein 2-thiazolecarboxamidine hydrochloride was replaced by 3-fluoropyridin-2-carboxamidine hydrochloride, and 2-chloro-4-fluorobenzaldehyde was replaced by 4-fluorobenzaldehyde to obtain a light yellow granule of 0.18 g (yield 25%). $^1$H-NMR (400 MHz, CDCl$_3$-d$_1$) δ 8.41 (m, 1H, ArH); 7.60-7.55 (m, 1H, ArH); 7.49-7.42 (m, 1H, ArH); 7.41-7.40 (m, 1H, ArH); 7.41-7.37 (t, 2H, J=8.8 Hz, ArH); 6.99-6.94 (t, 2H, J=8.8 Hz, ArH); 5.93 (s, 1H, CH); 2.69-2.62 (m, 2H, CH$_2$); 2.43-2.39 (m, 2H, CH$_2$); 2.09-2.06 (m, 2H, CH$_2$). HREI: 339.1187 (M$^+$).

Example 36

2-(3-fluoropyridin-2-yl)-4-(2-chlorophenyl)-7,8-dihydroquinazolin-5(1H)-one

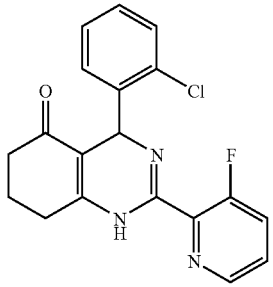

The method of Example 26 was used, wherein 2-thiazolecarboxamidine hydrochloride was replaced by 3-fluoropyridin-2-carboxamidine hydrochloride, and 2-chloro-4-fluorobenzaldehyde was replaced by 4-fluorobenzaldehyde to obtain a light yellow granule of 0.21 g (yield 27%). $^1$H-NMR (400 MHz, CDCl$_3$-d$_1$) δ 8.40-8.39 (d, 1H, J$_1$=1.2 Hz, ArH); 7.56-7.51 (t, 1H, J$_1$=1.2 Hz, J$_2$=8.4 Hz, ArH); 7.47-7.43 (m, 1H, J$_2$=8.4 Hz, ArH); 7.40-7.37 (m, 1H, ArH); 7.18-7.21 (m, 2H, ArH); 6.22 (s, 1H, CH); 2.90-2.67 (m, 2H, CH$_2$); 2.51-2.41 (m, 2H, CH$_2$); 2.19-2.12 (m, 2H, CH$_2$). MS (EI): 355.1 (M$^+$).

Example 37

2-(thiophen-2-yl)-4-(2-chloro-4-fluorophenyl)-7,7-dimethyl-7,8-dihydroquinazolin-5(1H)-one

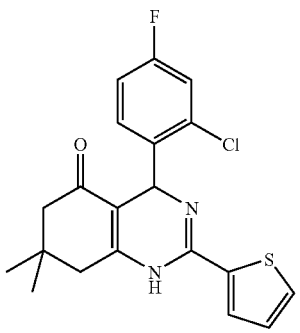

The method of Example 25 was used, wherein 2-thiazolecarboxamidine hydrochloride was replaced by 2-thiophenecarboxamidine hydrochloride to obtain a light yellow granule of 0.18 g (yield 22%). $^1$H-NMR (400 MHz, CDCl$_3$-d$_1$) δ 7.53-7.52 (d, 1H, J$_1$=4.0 Hz, ArH); 7.40 (m, 1H, ArH); 7.24-7.20 (t, 1H, J$_1$=2.4 Hz, J$_2$=8.0 Hz, ArH); 7.15-7.12 (dd, 1H, J$_1$=2.4 Hz, J$_2$=8.0 Hz, ArH); 7.08-7.06 (t, 1H, J$_1$=4.2 Hz, ArH); 6.94-6.90 (t, 1H, J$_1$=2.4 Hz, J$_2$=8.0 Hz, ArH); 6.02 (s, 1H, CH); 2.72-2.53 (m, 2H, CH$_2$); 2.30 (s, 2H, CH$_2$); 1.15 (s, 3H, CH$_3$); 1.14 (s, 3H, CH$_3$). HREI: 388.0812 (M).

Example 38

2-(thiophen-2-yl)-4-(2-chloro-4-fluorophenyl)-7,8-dihydroquinazolin-5(1H)-one

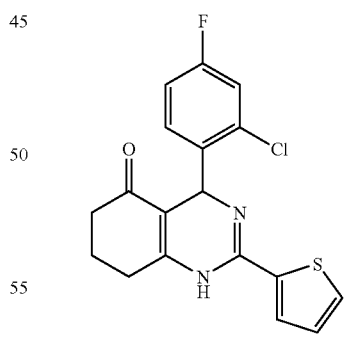

The method of Example 26 was used, wherein 2-thiazolecarboxamidine hydrochloride was replaced by 2-thiophenecarboxamidine hydrochloride to obtain a light yellow granule of 0.20 g (yield 26%). $^1$H-NMR (400 MHz, CDCl$_3$-d$_1$) δ 7.53-7.51 (d, 1H, J$_1$=5.2 Hz, ArH); 7.38 (s, 1H, ArH); 7.19-7.12 (m, 2H, ArH); 7.07-7.05 (t, 1H, J=5.2 Hz, ArH); 6.93-6.89 (t, 1H, J$_1$=2.4 Hz, J$_2$=8.0 Hz, ArH); 6.81 (s, 1H, NH); 6.00 (s, 1H, NH); 2.84-2.61 (m, 2H, CH$_2$); 2.50-2.38 (m, 2H, CH$_2$); 2.15-2.08 (m, 2H, CH$_2$). HREI: 360.0497 (M$^+$).

Example 39

Determination of Cytotoxicity and Antiviral Activity of the Compounds

The cytotoxicity and antiviral activity of the compounds according to the present invention were determined by the methods described above, and the results were shown in Table 1.

TABLE 1

Inhibition of the compounds on HBV DNA

| Ex. No. | IC$_{50}$ (μM) | TC$_{50}$ (μM) | SI |
|---|---|---|---|
| 1 | 0.026 | 109.01 | 4192 |
| 3 | 25.16 | 232.71 | 9.25 |
| 4 | 25.30 | 145.08 | 5.73 |
| 5 | 22.46 | 173.04 | 7.70 |
| 6 | >32.9 | 192.72 | <4.7 |
| 7 | 26.22 | 67.35 | 2.57 |
| 8 | >31.1 | 147.94 | <4.7 |
| 9 | >29.6 | 166.72 | <5.6 |
| 10 | >24.4 | 94.13 | <3.8 |
| 11 | >22.9 | 73.68 | <3.2 |
| 12 | >26.0 | 97.02 | <3.7 |

What is claimed is:

1. A compound of formula (I)

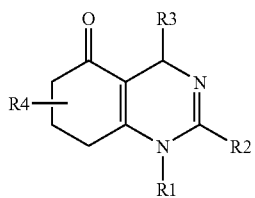

(I)

or an optical isomer thereof, or a pharmaceutically acceptable salt or hydrate thereof,
wherein
$R^1$ represents hydrogen, ($C_1$-$C_4$)-alkyl, ($C_2$-$C_4$)-alkenyl, ($C_2$-$C_6$)-acyl, sulfonyl or benzoyl,
$R^2$ represents a 5- or 6-membered aryl or heteroaryl mono-substituted or multiple-substituted with the same or different substituents selected from: hydrogen, halogen, hydroxyl, cyano, trifluoromethyl, nitro, benzyl, ($C_1$-$C_6$)-alkyl, ($C_1$-$C_6$)-alkoxyl, ($C_1$-$C_6$)-alkylthio, ($C_1$-$C_6$)-alkoxylcarbonyl, ($C_1$-$C_6$)-acyloxy, amino, ($C_1$-$C_6$)-alkylamino, ($C_1$-$C_6$)-dialkylamino, and ($C_1$-$C_6$)-acylamino,
$R^3$ represents an aryl or heteroaryl mono-substituted or multiple-substituted with the same or different substituents selected from: hydrogen, halogen, trifluoromethyl, trifluoromethoxyl, trifluoromethanesulfonyl, nitro, cyano, carboxyl, hydroxyl, ($C_1$-$C_6$)-alkoxyl, ($C_1$-$C_6$)-alkoxycarbonyl and ($C_1$-$C_6$)-alkyl, wherein the alkyl can be substituted with an aryl having 6-10 carbon atoms, halogen, or a group represented by —S—$R^5$, NR$^6$R$^7$, CO—NR$^8$R$^9$ or -A-CH$_2$—R$^{10}$,
wherein
$R^5$ represents phenyl which can be optionally substituted with halogen,
$R^6$, $R^7$, $R^8$ and $R^9$ are the same or different, and independently represents hydrogen, phenyl, hydroxyl-substituted phenyl, hydroxyl, ($C_1$-$C_6$)-acyl or ($C_1$-$C_6$)-alkyl, wherein the alkyl can be substituted with hydroxyl, halogen, ($C_1$-$C_6$)-alkoxycarbonyl, phenyl or hydroxyl-substituted phenyl,
A represents O, S, SO or SO$_2$,
$R^{10}$ represents phenyl optionally mono- or multiple-substituted with same or different substituents selected from: halogen, nitro, trifluoromethyl, ($C_1$-$C_6$)-alkyl and ($C_1$-$C_6$)-alkoxy, and
$R^4$ represents an optionally mono- or multiple-substituted, the same or different substituent selected from: hydrogen, halogen, nitro, cyano, hydroxyl, ($C_1$-$C_6$)-alkyl, ($C_1$-$C_6$)-alkoxyl, ($C_1$-$C_6$)-alkoxylcarbonyl, aryl and heteroaryl having 6-10 carbon atoms, wherein the aryl or heteroaryl can be substituted with halogen or ($C_1$-$C_6$)-alkyl.

2. The compound of formula (I) according to claim 1, or an optical isomer thereof, or a pharmaceutically acceptable salt or hydrate thereof,
wherein
$R^1$ represents hydrogen, methyl, acetyl, benzoyl or methylsulfonyl,
$R^2$ represents a 5- or 6-membered aryl or heteroaryl mono-substituted or multiple-substituted with the same or different substituents selected from: hydrogen, fluorine, chlorine, bromine, hydroxyl, cyano, trifluoromethyl, nitro, ($C_1$-$C_3$)-alkyl, ($C_1$-$C_3$)-alkoxyl, amino and ($C_1$-$C_3$)-acylamino,
$R^3$ represents an aryl or heteroaryl mono- or multiple-substituted with the same or different groups selected from: hydrogen, halogen, trifluoromethyl, trifluoromethoxyl, trifluoromethanesulfonyl, nitro, cyano, carboxyl, hydroxyl, methoxycarbonyl and a group represented by formula —CONHCH$_2$C(CH$_3$)$_3$, —CONH(CH$_2$)$_2$OH, —CONHCH$_2$C$_6$H$_5$, —CONHC$_6$H$_5$, —OCH$_2$C$_6$H$_5$ or —S-pCl—C$_6$H$_4$, and
$R^4$ represents an optionally mono- or multiple-substituted, the same or different substituent selected from: hydrogen, halogen, nitro, cyano, hydroxyl, ($C_1$-$C_3$)-alkyl, ($C_1$-$C_3$)-alkoxy, ($C_1$-$C_3$)-alkoxylcarbonyl, aryl and heteroaryl having 6-10 carbon atoms, wherein the aryl or heteroaryl can be substituted with halogen or ($C_1$-$C_3$)-alkyl.

3. The compound of formula (I) according to claim 1, or an optical isomer thereof, or a pharmaceutically acceptable salt or hydrate thereof,
wherein
$R^1$ represents hydrogen, acetyl or methylsulfonyl,
$R^2$ represents furyl, phenyl, pyridyl, or pyrazinyl optionally mono- or multiple-substituted with the same or different substituents selected from: hydrogen, fluorine, chlorine, bromine, trifluoromethyl, ($C_1$-$C_3$)-alkyl, ($C_1$-$C_3$)-alkoxyl, amino and ($C_1$-$C_3$)-acylamino,
$R^3$ represents phenyl optionally mono- or multiple-substituted with the same or different substituents selected from: hydrogen, fluorine, chlorine, bromine, trifluoromethyl, trifluoromethoxyl, trifluoromethanesulfonyl, nitro, cyano, carboxyl, hydroxyl and methoxycarbonyl, and
$R^4$ represents a substituent optionally mono- or multiple-substituted, the same or different substituent selected from: hydrogen, fluorine, chlorine, methyl, ethyl, propyl, isopropyl, methoxy, ethoxy, hydroxyl and phenyl, wherein the phenyl can be substituted with fluorine, chlorine or ($C_1$-$C_3$)-alkyl.

4. The compound of formula (I) according to claim 1, or an optical isomer thereof, or a pharmaceutically acceptable salt or hydrate thereof, wherein
R¹ represents hydrogen,
R² represents furyl, phenyl, pyridyl, or pyrazinyl optionally mono- or multiple-substituted with the same or different substituents selected from: hydrogen, and fluorine,
R³ represents phenyl optionally mono- or multiple-substituted with the same or different substituents selected from: hydrogen, chlorine, and fluorine, and
R⁴ represents a substituent optionally mono- or multiple-substituted, the same or different substituent selected from: hydrogen, and methyl.

5. The compound of formula (I) according to claim 1, having the following structures,
- 2-(pyridin-3-yl)-4-(2-chloro-4-fluorophenyl)-7,7-dimethyl-4,6,7,8-tetrahydroquinazolin-5(1H)-one,
- 2-(pyridin-3-yl)-4-(2-chloro-4-fluorophenyl)-7,7-dimethyl-4,6,7,8-tetrahydroquinazolin-5(1H)-one hydrochloride,
- 2-(pyridin-3-yl)-4-(2-chloro-4-fluorophenyl)-4,6,7,8-tetrahydroquinazolin-5(1H)-one,
- 2-(pyridin-3-yl)-4-(4-fluorophenyl)-7,7-dimethyl-4,6,7,8-tetrahydroquinazolin-5(1H)-one,
- 2-(pyridin-3-yl)-4-phenyl-7,7-dimethyl-4,6,7,8-tetrahydroquinazolin-5(1H)-one,
- 2-(pyridin-3-yl)-4-phenyl-4,6,7,8-tetrahydroquinazolin-5 (1H)-one,
- 2-(pyridin-3-yl)-4-(2-chlorophenyl)-7,7-dimethyl-4,6,7,8-tetrahydroquinazolin-5(1H)-one,
- 2-(pyridin-3-yl)-4-(4-fluorophenyl)-4,6,7,8-tetrahydroquinazolin-5(1H)-one,
- 2-(pyridin-3-yl)-4-(2-chlorophenyl)-4,6,7,8-tetrahydroquinazolin-5(1H)-one,
- 2-(2,4,6-trifluorophenyl)-4-(2-chloro-4-fluorophenyl)-4,6,7,8-tetrahydroquinazolin-5(1H)-one,
- 2-(2,4,6-trifluorophenyl)-4-(2-chloro-4-fluorophenyl)-7,7-dimethyl-4,6,7,8-tetrahydroquinazolin-5 (1H)-one,
- 2-(pyridin-2-yl)-4-(2-chloro-4-fluorophenyl)-7,7-dimethyl-4,6,7,8-tetrahydroquinazolin-5 (1H)-one,
- 2-(pyrazin-2-yl)-4-(2-chloro-4-fluorophenyl)-7,7-dimethyl-4,6,7,8-tetrahydroquinazolin-5(1H)-one,
- 2-(pyrazin-2-yl)-4-(2-chlorophenyl)-7,7-dimethyl-4,6,7,8-tetrahydroquinazolin-5(1H)-one,
- 2-(pyrazin-2-yl)-4-(2-chloro-4-fluorophenyl)-4,6,7,8-tetrahydroquinazolin-5(1H)-one,
- 2-(pyrazin-2-yl)-4-(2-chlorophenyl)-4,6,7,8-tetrahydroquinazolin-5(1H)-one,
- 2-(3-fluoropyridin-2-yl)-4-(2-chloro-4-fluorophenyl)-7,7-dimethyl-4,6,7,8-tetrahydroquinazolin-5(1H)-one,
- 2-(3-fluoropyridin-2-yl)-4-(2-chloro-4-fluorophenyl)-4,6,7,8-tetrahydroquinazolin-5(1H)-one,
- 2-(furan-2-yl)-4-(2-chloro-4-fluorophenyl)-7,7-dimethyl-4,6,7,8-tetrahydroquinazolin-5(1H)-one,
- 2-(furan-2-yl)-4-(2-chloro-4-fluorophenyl)-4,6,7,8-tetrahydroquinazolin-5(1H)-one,
- 2-(pyridin-2-yl)-4-(2-chloro-4-fluorophenyl)-4,6,7,8-tetrahydroquinazolin-5(1H)-one,
- 2-(pyridin-2-yl)-4-(2-chlorophenyl)-4,6,7,8-tetrahydroquinazolin-5(1H)-one,
- 2-(pyridin-2-yl)-4-(4-fluorophenyl)-4,6,7,8-tetrahydroquinazolin-5(1H)-one,
- 2-(pyridin-2-yl)-4-phenyl-4,6,7,8-tetrahydroquinazolin-5 (1H)-one,
- 2-(thiazol-2-yl)-4-(2-chloro-4-fluorophenyl)-7,7-dimethyl-7,8-dihydroquinazolin-5(1H)-one,
- 2-(thiazol-2-yl)-4-(2-chloro-4-fluorophenyl)-7,8-dihydroquinazolin-5(1H)-one,
- 2-(thiazol-2-yl)-4-(4-fluorophenyl)-7,8-dihydroquinazolin-5(1H)-one,
- 2-(thiazol-2-yl)-4-(2-chlorophenyl)-7,8-dihydroquinazolin-5(1H)-one,
- 2-(thiazol-2-yl)-4-(2-chloro-4-fluorophenyl)-7,7-dimethyl-7,8-dihydroquinazolin-5(1H)-one,
- 2-(pyridin-4-yl)-4-(2-chloro-4-fluorophenyl)-7,7-dimethyl-7,8-dihydroquinazolin-5(1H)-one,
- 2-(pyridin-4-yl)-4-(2-chloro-4-fluorophenyl)-7,8-dihydroquinazolin-5(1H)-one,
- 2-(3,5-difluoropyridin-2-yl)-4-(2-chloro-4-fluorophenyl)-7,7-dimethyl-7,8-dihydroquinazolin-5 (1H)-one,
- 2-(3,5-difluoropyridin-2-yl)-4-(2-chloro-4-fluorophenyl)-7,8-dihydroquinazolin-5(1H)-one,
- 2-(3-fluoropyridin-2-yl)-4-(4-fluorophenyl)-7,7-dimethyl-7,8-dihydroquinazolin-5(1H)-one,
- 2-(3-fluoropyridin-2-yl)-4-(4-fluorophenyl)-7,8-dihydroquinazolin-5(1H)-one,
- 2-(3-fluoropyridin-2-yl)-4-(2-chlorophenyl)-7,8-dihydroquinazolin-5(1H)-one,
- 2-(thiophen-2-yl)-4-(2-chloro-4-fluorophenyl)-7,7-dimethyl-7,8-dihydroquinazolin-5(1H)-one,
- 2-(thiophen-2-yl)-4-(2-chloro-4-fluorophenyl)-7,8-dihydroquinazolin-5(1H)-one, an optical isomer thereof, a pharmaceutically acceptable salt, or a hydrate thereof.

6. A process for preparing a compound according to claim 4, comprising:
reacting an amidine of formula (II) or a salt thereof

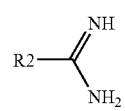

wherein R² represents furyl, phenyl, pyridyl, or pyrazinyl optionally mono- or multiple-substituted with the same or different substituents selected from: hydrogen, and fluorine,
with an aldehyde of formula (III)

wherein R³ represents phenyl optionally mono- or multiple-substituted with the same or different substituents selected from: hydrogen, chlorine, and fluorine,
and with a compound of formula (IV),

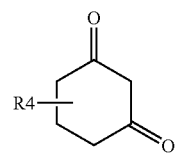

wherein R⁴ represents a substituent optionally mono- or multiple-substituted, the same or different substituent selected from: hydrogen, and methyl,
at 20-150° C. in a suitable inert solvent in the presence or absence of a base or an acid;

or reacting a compound of formula (V) or (VI)

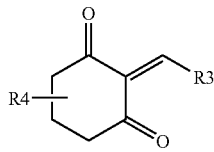
(V)

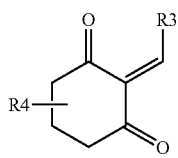
(VI)

wherein R³ represents phenyl optionally mono- or multiple-substituted with the same or different substituents selected from: hydrogen, chlorine, and fluorine, and R⁴ represents a substituent optionally mono- or multiple-substituted, the same or different substituent selected from: hydrogen, and methyl, with the compound of formula (II)

at 20-150° C., in a suitable inert solvent, in the presence or absence of abase or acid;

to obtain the compound of claim 4.

7. A pharmaceutical composition, comprising a compound of formula (I) according to claim 1, an optical isomer thereof, a pharmaceutically acceptable salt thereof, or hydrate thereof, and at least one pharmaceutically acceptable carrier, and optionally, further comprising another pharmaceutically active compound.

8. A method for treating an acute or chronic infection caused by hepatitis B virus, the method comprising administering the compound of formula (I) according to claim 1, an optical isomer thereof, a pharmaceutically acceptable salt, or a hydrate thereof to a subject in need thereof.

9. A process for preparing a compound according to claim 5, comprising:

reacting an amidine of formula (II) or a salt thereof

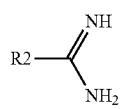
(II)

wherein R² represents furyl, phenyl, pyridyl, or pyrazinyl optionally mono- or multiple-substituted with the same or different substituents selected from: hydrogen, and fluorine, with an aldehyde of formula (III)

R³CHO    (III)

wherein R³ represents phenyl optionally mono- or multiple-substituted with the same or different substituents selected from: hydrogen, chlorine, and fluorine and with a compound of formula (IV),

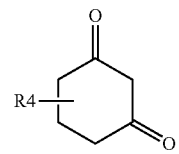
(IV)

wherein R⁴ represents a substituent optionally mono- or multiple-substituted, the same or different substituent selected from: hydrogen, and methyl, at 20-150° C. in a suitable inert solvent in the presence or absence of a base or an acid;

or reacting a compound of formula (V) or (VI)

(V)

(VI)

wherein R³ represents phenyl optionally mono- or multiple-substituted with the same or different substituents selected from: hydrogen, chlorine, and fluorine, and R⁴ represents a substituent optionally mono- or multiple-substituted, the same or different substituent selected from: hydrogen, and methyl, with the compound of formula (II)

at 20-150° C., in a suitable inert solvent, in the presence or absence of abase or acid;

to obtain the compound of claim 5.

10. A pharmaceutical composition, comprising a compound of formula (I) according to claim 2, an optical isomer thereof, a pharmaceutically acceptable salt thereof, or hydrate thereof, and at least one pharmaceutically acceptable carrier, and optionally, further comprising another pharmaceutically active compound.

11. A pharmaceutical composition, comprising a compound of formula (I) according to claim 3, an optical isomer thereof, a pharmaceutically acceptable salt thereof, or hydrate thereof, and at least one pharmaceutically acceptable carrier, and optionally, further comprising another pharmaceutically active compound.

12. A pharmaceutical composition, comprising a compound of formula (I) according to claim 4, an optical isomer thereof, a pharmaceutically acceptable salt thereof, or hydrate thereof, and at least one pharmaceutically acceptable carrier, and optionally, further comprising another pharmaceutically active compound.

13. A pharmaceutical composition, comprising a compound of formula (I) according to claim 5, an optical isomer thereof, a pharmaceutically acceptable salt thereof, or hydrate thereof, and at least one pharmaceutically acceptable carrier, and optionally, further comprising another pharmaceutically active compound.

14. A method for treating an acute or chronic infection caused by hepatitis B virus, the method comprising administering the compound of formula (I) according to claim 2, an optical isomer thereof, a pharmaceutically acceptable salt, or a hydrate thereof to a subject in need thereof.

15. A method for treating an acute or chronic infection caused by hepatitis B virus, the method comprising administering the compound of formula (I) according to claim 3, an optical isomer thereof, a pharmaceutically acceptable salt, or a hydrate thereof to a subject in need thereof.

16. A method for treating an acute or chronic infection caused by hepatitis B virus, the method comprising administering the compound of formula (I) according to claim 4, an optical isomer thereof, a pharmaceutically acceptable salt, or a hydrate thereof to a subject in need thereof.

17. A method for treating an acute or chronic infection caused by hepatitis B virus, the method comprising administering the compound of formula (I) according to claim 5, an optical isomer thereof, a pharmaceutically acceptable salt, or a hydrate thereof to a subject in need thereof.

* * * * *

UNITED STATES PATENT AND TRADEMARK OFFICE
CERTIFICATE OF CORRECTION

| | | |
|---|---|---|
| PATENT NO. | : 8,188,091 B2 | Page 1 of 1 |
| APPLICATION NO. | : 12/523215 | |
| DATED | : May 29, 2012 | |
| INVENTOR(S) | : Song Li et al. | |

It is certified that error appears in the above-identified patent and that said Letters Patent is hereby corrected as shown below:

Title Page, Item (54), and Column 1, line 1, Title "TETRAHYDROQUINAZOLINE" should read

--TETRAHYDROQUINAZOLINONE--.

Column 11, line 24, (first occurrence) "H" should read --II--.

Column 11, line 58, "(volume 25 p. 1)." should read --(volume 25μ1).--.

Column 13, line 9, "chronicle," should read --chronical,--.

Column 20, line 34, "2.48-2.72 m," should read --2.48-2.72--.

Column 20, line 35, "CH$_2$);" should read --2H, m, CH$_2$)--.

Column 21, line 16, "3-pyridinec:" should read --3-pyridinec--.

Column 26, line 63, "(Schaefer P.C." should read --Schaefer F.C.,--.

Column 36, line 66, "20-150° C." should read --20-150° C,--.

Column 37, line 29, "20-150° C.," should read --20-150° C,--.

Column 37, line 30, "abase" should read --a base--.

Column 38, line 14, "20-150° C.," should read --20-150° C,--.

Column 38, line 41, "20-150° C.," should read --20-150° C,--.

Column 38, line 42, "abase" should read --a base--.

Signed and Sealed this
Second Day of October, 2012

David J. Kappos
*Director of the United States Patent and Trademark Office*